United States Patent
Breton et al.

(10) Patent No.: US 9,317,657 B2
(45) Date of Patent: Apr. 19, 2016

(54) METHOD, SYSTEM, AND COMPUTER PROGRAM PRODUCT FOR TRACKING OF BLOOD GLUCOSE VARIABILITY IN DIABETES

(75) Inventors: Marc D. Breton, Charlottesville, VA (US); Boris P. Kovatchev, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1174 days.

(21) Appl. No.: 13/131,467

(22) PCT Filed: Nov. 24, 2009

(86) PCT No.: PCT/US2009/065725
§ 371 (c)(1),
(2), (4) Date: Jul. 18, 2011

(87) PCT Pub. No.: WO2010/062898
PCT Pub. Date: Jun. 3, 2010

(65) Prior Publication Data
US 2011/0264378 A1    Oct. 27, 2011

Related U.S. Application Data

(60) Provisional application No. 61/118,022, filed on Nov. 26, 2008, provisional application No. 61/260,116, filed on Nov. 11, 2009.

(51) Int. Cl.
*G06F 19/00* (2011.01)
*G01N 33/48* (2006.01)
(Continued)

(52) U.S. Cl.
CPC .......... *G06F 19/3406* (2013.01); *A61B 5/0002* (2013.01); *A61B 5/14532* (2013.01); *A61B 5/7275* (2013.01); *G06F 19/345* (2013.01); *G06F 19/363* (2013.01)

(58) Field of Classification Search
CPC ... G06F 19/00; G06F 19/363; G06F 19/3406; G06F 19/345; A61B 5/0002; A61B 5/7275; A61B 5/14532
USPC ................................ 702/19, 26; 700/266, 17
See application file for complete search history.

(56) References Cited

U.S. PATENT DOCUMENTS 8,010,174 B2 *   8/2011   Goode et al. ................... 600/347
8,409,093 B2 *   4/2013   Bugler ............... A61B 5/14532
                                                          600/347

(Continued)

FOREIGN PATENT DOCUMENTS

EP          1933246 A1     6/2008

OTHER PUBLICATIONS

Kovatchev et al., "Evaluation of a New Measure of Blood Glucose Variability in Diabetes," Diabetes Care, Nov. 2006, vol. 29, No. 11, pp. 2433-2438.

*Primary Examiner* — Carol S. W. Tsai
(74) *Attorney, Agent, or Firm* — Vorys, Sater, Seymour and Pease LLP; Vincent M DeLuca; Robert J Decker

(57) ABSTRACT

An embodiment may be in the field of glycemic analysis and control. More specifically, an embodiment or approach may provide a novel method, system, and computer program for the visual and quantitative tracking of blood glucose variability in diabetes from self-monitoring blood glucose (SMBG) data and/or continuous glucose monitoring (CGM) data. More particularly, an embodiment or aspects thereof may use glucose measurements obtained from self-monitoring data and/or CGM data of an individual or a group of individuals to track and analyze blood glucose variability.

57 Claims, 25 Drawing Sheets

(51) Int. Cl.
*A61B 5/00* (2006.01)
*A61B 5/145* (2006.01)

(56) References Cited

U.S. PATENT DOCUMENTS

| | | | | |
|---|---|---|---|---|
| 8,761,940 | B2* | 6/2014 | Long | G06F 19/3406 600/365 |
| 2002/0150070 | A1* | 10/2002 | Shattil | 370/342 |
| 2003/0195404 | A1* | 10/2003 | Knobbe et al. | 600/365 |
| 2004/0034295 | A1* | 2/2004 | Salganicoff | 600/365 |
| 2005/0214892 | A1 | 9/2005 | Kovatchev et al. | |
| 2005/0277164 | A1* | 12/2005 | Drucker et al. | 435/14 |
| 2006/0167365 | A1* | 7/2006 | Bharmi | 600/517 |
| 2007/0010950 | A1 | 1/2007 | Abensour et al. | |
| 2007/0016127 | A1 | 1/2007 | Staib et al. | |
| 2007/0025421 | A1* | 2/2007 | Shattil | 375/136 |
| 2007/0232878 | A1* | 10/2007 | Kovatchev et al. | 600/365 |
| 2007/0258707 | A1* | 11/2007 | Raskar | 396/52 |
| 2008/0154513 | A1* | 6/2008 | Kovatchev et al. | 702/19 |
| 2008/0208027 | A1* | 8/2008 | Heaton | 600/365 |
| 2008/0311968 | A1* | 12/2008 | Hunter | 463/1 |
| 2009/0030617 | A1* | 1/2009 | Schell et al. | 702/19 |
| 2009/0043541 | A1* | 2/2009 | Brauker et al. | 702/189 |
| 2009/0048503 | A1* | 2/2009 | Dalal et al. | 600/365 |
| 2009/0105568 | A1* | 4/2009 | Bugler | A61B 5/1495 600/347 |
| 2009/0192380 | A1* | 7/2009 | Shariati et al. | 600/365 |
| 2009/0192751 | A1* | 7/2009 | Kamath et al. | 702/104 |
| 2009/0240127 | A1 | 9/2009 | Ray | |
| 2010/0074532 | A1* | 3/2010 | Gordon et al. | 382/203 |
| 2010/0152554 | A1* | 6/2010 | Steine et al. | 600/309 |
| 2010/0179768 | A1* | 7/2010 | Kovatchev et al. | 702/19 |
| 2010/0312176 | A1* | 12/2010 | Lauer et al. | 604/66 |
| 2011/0053121 | A1* | 3/2011 | Heaton | 434/127 |
| 2012/0095310 | A1* | 4/2012 | Long | G06F 19/3406 600/365 |
| 2012/0266251 | A1* | 10/2012 | Birtwhistle | G06F 19/323 726/26 |
| 2013/0172706 | A1* | 7/2013 | Carlsgaard | A61B 5/743 600/365 |
| 2013/0225959 | A1* | 8/2013 | Bugler | A61B 5/1495 600/365 |
| 2014/0100435 | A1* | 4/2014 | Duke | G06F 19/3431 600/365 |
| 2015/0230741 | A1* | 8/2015 | Bugler | A61B 5/14532 600/365 |

* cited by examiner

The VGA window on start up.

METHOD, SYSTEM, AND COMPUTER PROGRAM PRODUCT FOR TRACKING OF BLOOD GLUCOSE VARIABILITY IN DIABETES

RELATED APPLICATIONS

The present application claims priority from U.S. Provisional Application Ser. No. 61/118,022, filed Nov. 26, 2008, entitled "Method, System, and Computer Program Product for Visual and Quantitative Tracking of Blood. Glucose Variability in Diabetes from Self-Monitoring Data" and U.S. Provisional Application Ser. No. 61/260,116, filed Nov. 11, 2009, entitled "Method, System, and Computer Program Product for Visual and Quantitative Tracking of Blood Glucose Variability in Diabetes from Blood Glucose Data;" the disclosures of which are hereby incorporated by reference herein in their entirety.

GOVERNMENT SUPPORT

Work described herein was supported by Federal Grant No. ONR Grant No. R01 DK51562, awarded by National Institute of Health (NIH). The Government has certain rights in the invention.

FIELD OF THE INVENTION

Some aspects of some embodiments this invention are in the field of glycemic analysis and control. More specifically, some embodiments of the invention provides a novel method, system, and computer program for the visual and quantitative tracking of blood glucose variability in diabetes from self-monitoring blood glucose (SMBG) data and/or continuous glucose monitoring (CGM) data. More particularly, some embodiments of the invention or aspects thereof use glucose measurements obtained from self-monitoring (SMBG) data and/or CGM data of an individual or a group of individuals to track and analyze blood glucose variability.

BACKGROUND OF THE INVENTION

The Importance of Blood Glucose Variability in Diabetes

HbA1c is the classic marker of glycemic status, introduced 23 years ago [1], linked to diabetes complications, and confirmed as the gold standard measure of average glycemic control in Type 1 and Type 2 diabetes (T1DM and T2DM), [2, 3, 4]. However, in addition to establishing HbA1c, the Diabetes Control and Complications Trial (DCCT) concluded that: "HbA1c is not the most complete expression of the degree of glycemia. Other features of diabetic glucose control, which are not reflected by HbA1c, may add to, or modify the risk of complications. For example, the risk of complications may be more highly dependent on the extent of post-prandial glycemic excursions." [5]. Consequently, contemporary studies increasingly concentrate on the variability of blood glucose (BG) fluctuations as an independent factor for diabetes complications [6]. Two prominent manifestations of glycemic variability are hypoglycemia and postprandial glucose (PPG) elevation.

Hypoglycemia: Hypoglycemia is common in T1DM [7] and becomes more prevalent in T2DM with treatment intensification [8]. Hypoglycemia-associated autonomic failure (HAAF) is well documented in T1DM [9] and is observed in intensively treated T2DM as well [10]. Even state-of-the-art therapies are imperfect and may trigger acute lowering of BG levels, potentially leading to severe hypoglycemia (SH), defined as severe neuroglycopenia resulting in unconsciousness or stupor that precludes self-treatment [7]. SH may cause cognitive dysfunction, coma, or sudden death [7,11]. Consequently, hypoglycemia has been identified as the primary barrier to optimal diabetes management [12].

Hyperglycemia and PPG Excursions: In health, PPG fluctuations are limited in both their peak value, rarely exceeding 11 mmol/l, and in their duration, with a peak PPG at approximately 1 hour after the start of a meal and return to preprandial levels within 2-3 hours [13]. In diabetes, a number of factors, such as insulin resistance, inadequate available insulin, delayed insulin action, or abnormalities in glucagon secretion, contribute to delayed peak PPG, and higher and prolonged PPG elevation [13]. While in T1DM PPG excursions depend to certain degree on physiology, their control is almost entirely behavioral, depending on the amount and timing of pre-meal insulin bolus, as well as on the degree of physical activity. In non-insulin treated T2DM, prolonged extreme PPG results from insulin resistance that is not compensated by β-cell response. Specifically, in early T2DM the first phase of insulin response to meal is blunted, while the total insulin response is similar to health [14].

Measures of Blood Glucose Variability

Standard Deviation (SD) and Other Variability Measures: The traditional statistical calculation of BG variability includes computing the SD of BG readings as well as several other measures: (i) The M-value introduced in 1965 [15]; (ii) MAGE—Mean Amplitude of Glucose Excursions—introduced in 1970 [16], and (iii) the Lability Index (LI)—a recently developed measure of hypoglycemia and glycemic lability [17]. Most of these measures (except the LI) have a relatively weak association with hypoglycemia and an inherent bias towards hyperglycemia, which is reflected by the historically poor prediction of SH [7]. In previous studies, we have found that there may exist an aspect of poor prediction [18]. Clinical conclusions based on numerical methods, will be less accurate for the constricted hypoglycemic range and will be biased towards hyperglycemia.

Analyzing the amplitude of BG excursions: In order to correct the numerical problem created by the asymmetry of the BG scale we have introduced a mathematical transformation that symmetrizes the BG scale [18]. It is important to note that the analytical form of this transformation is based on accepted clinical assumptions, not on a particular data set, and has been fixed ten years ago [18], which makes the approach extendable to any data set. Based on this transformation, we have developed our theory of risk analysis of BG data [21] that defines a computational risk space that proved to be very suitable for quantifying the extent and frequency of glucose excursions. In essence, analysis in risk space entails converting first each BG reading into a risk value using two steps: (i) application of the symmetrization formula [18], and (ii) application of a quadratic risk function that assigns increasing weights to larger BG deviations towards hypoglycemia or hyperglycemia [21]. Recently we have introduced a new risk-based measure of glucose variability—the Average Daily Risk Range (ADRR), which has been shown superior to traditional measures in terms of risk assessment and prediction of extreme glycemic excursions [25].

Continuous Glucose Monitoring (CGM)

Continuous Glucose Monitors (CGM) generate data streams that have the potential to revolutionize the opportunities for reducing the extremes of blood glucose (BG) levels that characterize glycemia in T1DM. Such data, however, are both voluminous and complex, and their analysis requires an understanding of the physical, biochemical, and mathematical principles and properties involved in this new technology. Other articles describe the physical and biochemical parameters associated with CGM.

BRIEF SUMMARY OF THE INVENTION

An aspect of an embodiment or partial embodiment of the present invention (or combinations of various embodiments in whole or in part of the present invention) comprises, but not limited thereto, a method and system (and related computer program product) for visual and quantitative tracking of blood glucose variability from routine self-monitoring (SMBG) and/or continuous-monitoring (CGM) data in a group of patients with diabetes or at an individual level. The method (and related system and computer program product) is based on a specific Variability Grid Analysis (VGA), which can be used for two functions:

1. To present glucose variability and the extent of glycemic fluctuations at a group level, which is suitable for tracking populations and review of clinical trial results; and/or
2. To track the glucose variability of a single person by plotting a trajectory of data points on a weekly basis, which is suitable for making individualized treatment decisions and for alerting physicians whenever important thresholds are approached.

The system retrieves the data from a data source—typically a set of SMBG and/or CGM data of a person downloaded from the person's meter—and allows tracking of glucose variability and extreme glycemic events. The tracking includes presentation of visual and numerical output based on the VGA, as well as reconstruction of trajectories that would enable messages warning for crossing of predefined thresholds, such as boundaries between VGA zones. A primary operation mode of the system may be for tracking of a population or a person over time. Another application may be comparison of population snapshots across time, which will allow testing of various treatment outcomes.

Experimental software has been developed (using MAT-LAB®) to illustrate one variant of the VGA method—the Min/Max VGA. The software allows for displaying individual trajectories and populations to illustrate the concept of glucose variability tracking, and includes extraction and tracking over time at an individual level of relevant characteristics of glucose variability and associated hypoglycemic and hyperglycemic extremes.

An aspect of an embodiment of the present invention provides a system for visually tracking blood glucose variability in diabetes in a subject. The system may comprise: an acquisition module acquiring a plurality of blood glucose data; and a processor programmed to track blood glucose variability based on the blood glucose data. The tracking may provide an area(s) of optimal glucose control in a plane; and an area(s) indicating risk for hyperglycemia and hypoglycemia in the plane.

It should be appreciated that any of the embodiments discussed herein may be intended for some sort or kind of visual tracking. However, it should be appreciated that information that is conveyed visually may be conveyed audibly and/or tactically (perceptible to the sense of touch) if desired or required. Accordingly, a audible and/or tactile scheme would be provided to convey or provide at least some or all of the aspects being conveyed visually or in combination therewith. Moreover, for example, audible signals may be provided in addition to or in concert or parallel with the visual information.

Therefore, it should be appreciated that the embodiment of the system may involve a plane that may be two-dimensional, as well as be a three-dimensional arrangement or module. Moreover, it should be appreciated that the visual tracking may be replaced with audible and/or tactile tracking, or the audible and/or tactile tracking may be provided in addition to the visual tracking.

An aspect of an embodiment of the present invention provides a method for visually tracking blood glucose variability in diabetes in a subject. The method may comprise: acquiring a plurality of blood glucose data and tracking blood glucose variability based on the blood glucose data. The tracking may provide an area(s) of optimal glucose control in a plane; and an area(s) indicating risk for hyperglycemia and hypoglycemia in the plane. It should be appreciated that the plane may be two-dimensional, as well as be a three-dimensional arrangement or module. Moreover, it should be appreciated that the visual tracking may be replaced with audible and/or tactile tracking, or the audible and/or tactile tracking may be provided in addition to the visual tracking.

An aspect of an embodiment of the present invention provides a computer program product comprising a computer useable medium having a computer program logic for enabling at least one processor in a computer system to track blood glucose variability in diabetes in a subject, or in a group of subjects. The computer program logic may comprise: acquiring a plurality of blood glucose data; and tracking blood glucose variability based on the blood glucose data. The tracking may provide an area(s) of optimal glucose control intended for a plane format or three-dimensional format (as well as audible and/or tactile format) and an area(s) indicating risk for hyperglycemia and hypoglycemia in the plane format or three-dimensional format (as well as audible and/or tactile format).

An aspect of an embodiment of the present invention provides a system for audibly tracking blood glucose variability in diabetes in a subject. The system may comprise: an acquisition module acquiring a plurality of blood glucose data; and a processor programmed to track blood glucose variability based on said blood glucose data. The tracking may provide a signal(s) for optimal glucose control; and signals indicating risk for hyperglycemia and hypoglycemia.

An aspect of an embodiment of the present invention provides a method for audibly tracking blood glucose variability in diabetes in a subject. The method may comprise: acquiring a plurality of blood glucose data; tracking blood glucose variability based on said blood glucose data. The tracking may provide a signal(s) of optimal glucose control; and signals indicating risk for hyperglycemia and hypoglycemia.

These and other objects, along with advantages and features of various aspects of embodiments of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings The accompanying drawings, which are incorporated into and form a part of the instant specification, illustrate several aspects and embodiments of the present invention and, together with the description herein, serve to explain the principles of the invention. The drawings are provided only

DETAILED DESCRIPTION OF THE INVENTION

Example Embodiments

Figure 1:
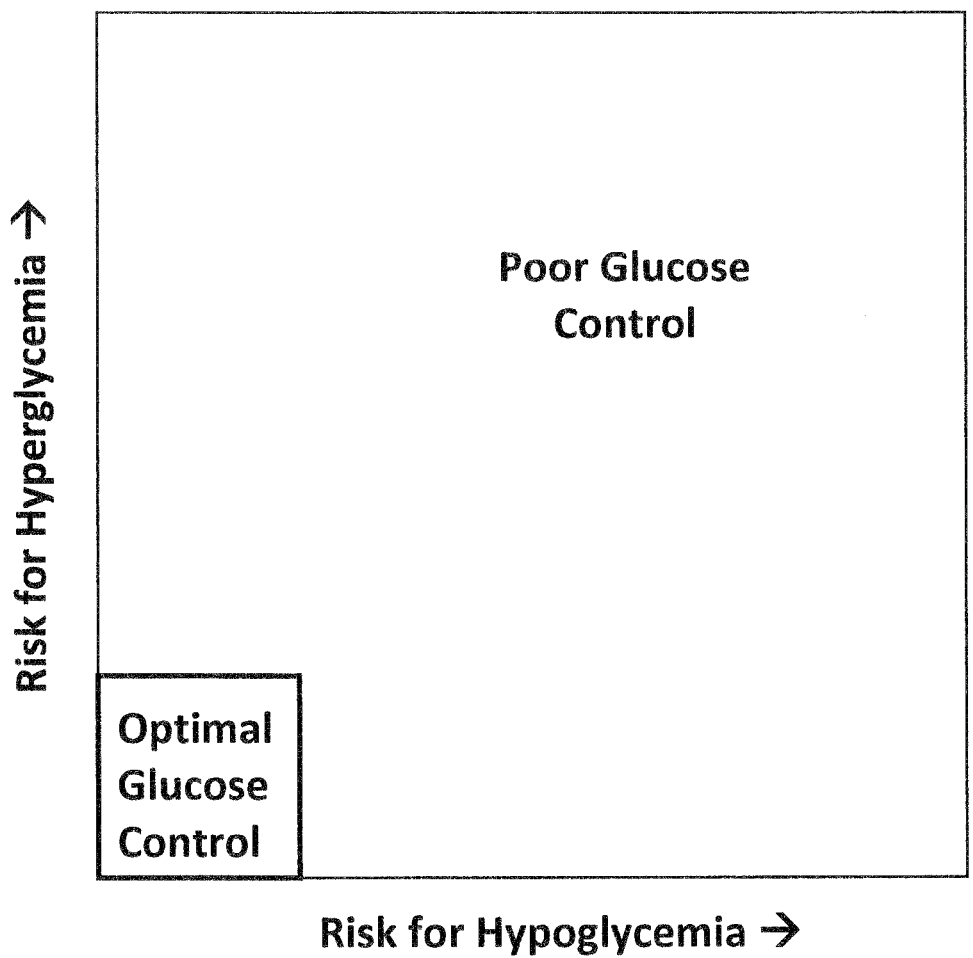
FIG. 1: Provides an embodiment of the Risk for Hypoglycemia and Risk for Hyperglycemia plane with optimal glucose control zone.

FIG. 1 depicts an aspect of an embodiment of the present invention. In FIG. 1, one axis represents the risk for hypoglycemia and a second axis represents the risk for hyperglycemia. Furthermore, in FIG. 1, there is one zone which represents optimal glucose control and there is another zone which represents poor glucose control.

Figure 2:
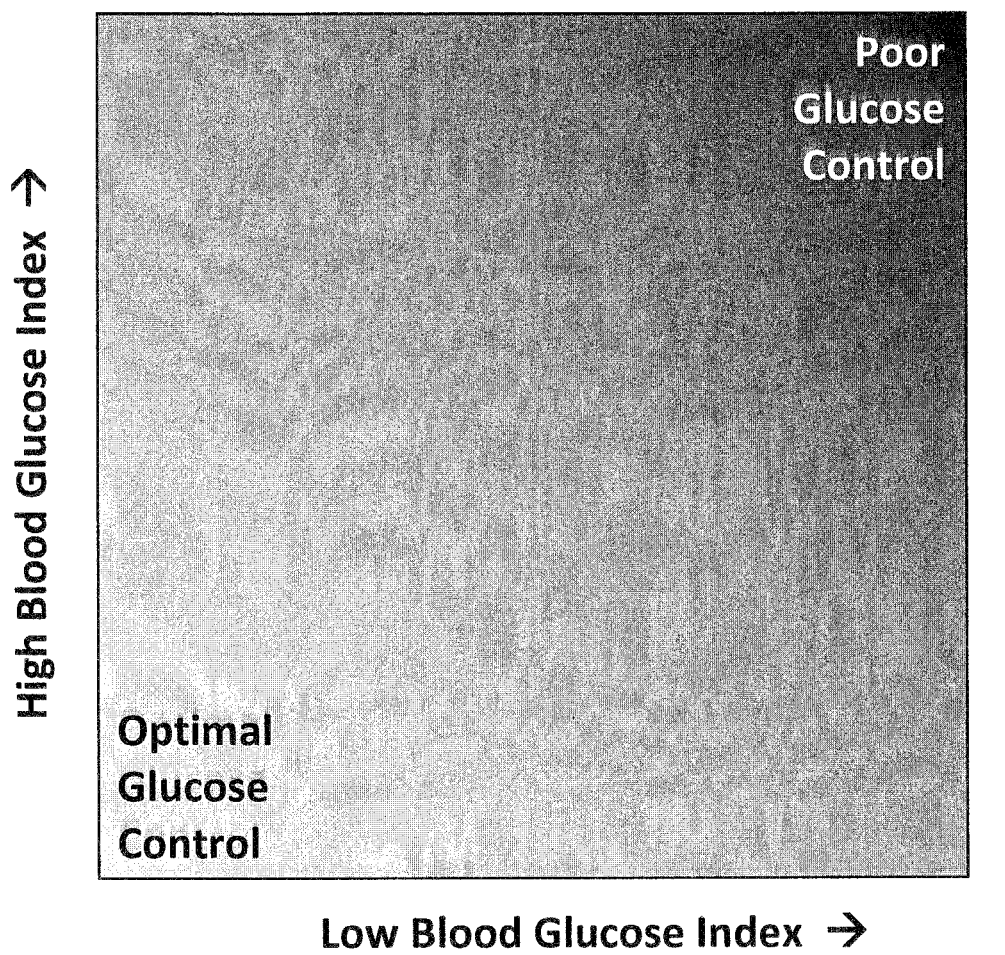
FIG. 2: Provides an embodiment of the Low Blood Glucose Index and High Blood Glucose Index plane with optimal glucose control zone.

FIG. 2 depicts an aspect of an embodiment of the present invention. In FIG. 2, one axis represents the Low Blood Glucose Index and a second axis represents the High Blood Glucose Index. Furthermore, in FIG. 2, there is one zone which represents optimal glucose control and there is a gradient which represents increasing poor glucose control.

Figure 3:
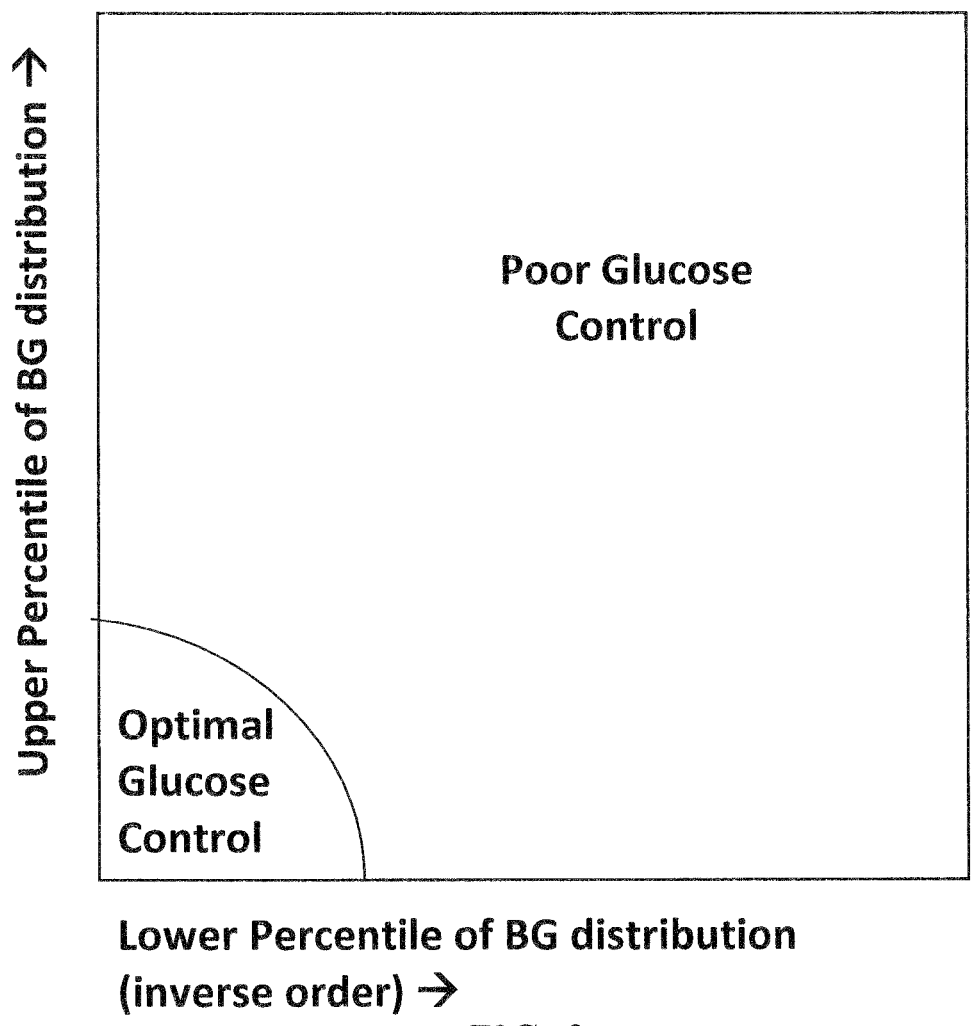
FIG. 3: Provides an embodiment of the Lower Percentile and Upper Percentile plane with optimal glucose control zone.

FIG. 3 depicts an aspect of an embodiment of the present invention. In FIG. 3, one axis represents the inverse coded lower percentile and a second axis represents the higher percentile. Furthermore, in FIG. 3, there is one zone which represents optimal glucose control and there is another zone which represents poor glucose control.

It should be appreciated that the axes discussed throughout this disclosure may be reversed in some embodiments of the present invention. Additionally, it should be appreciated that the zones discussed throughout this disclosure may vary in number, size, space, quantity, and/or contours (two-dimensionally and three-dimensionally) in at least some embodiments of the present invention. Furthermore, it should be appreciated that the relative size or each zone may vary in at least some embodiments of the present invention.

Moreover, it should be appreciated that besides two-dimension X-Y planes, the plane may further be adapted to be entire continual geometric spectrum of manipulation of x, y and z planes. In such case, for example, the appearance may be contoured having a three-dimensional feature to it.

It should be appreciated that the tracking to determine the extent of glycemic fluctuations, glucose variability, or glucose events over a specified time interval will be applied as desired or required. For example, but not limited thereto, the time intervals and durations may be any combination of at least one of the following: approximately weekly, greater than weekly, less than weekly, two or more days, approximately daily, less than daily, approximately a half day, approximately two or more hours, approximately an hour, less than an hour, or approximately fifteen minutes.

Graphical Introduction of the Variability-Grid Analysis (VGA)

Because the magnitude of glucose variability and the risks for hypoglycemia and hyperglycemia are tightly related [25], an aspect of the VGA is to classify the SMBG data and/or CGM data of a subject along two principal axes: risk for hypoglycemia and risk for hyperglycemia. Then the hypo-hyperglycemia plane is divided into zones representing various degrees of variability control:

A-zone—Optimal control of glucose variability;

Lower B—Moderate deviations into hypoglycemia, but good control of hyperglycemia;

Upper B—Moderate deviations into hyperglycemia, but good control of hypoglycemia;

B-zone—Moderate deviations towards both hypo- and hyperglycemia;

Lower C—Over-Correction of hyperglycemia;

Upper C—Over-Correction of hypoglycemia;

Lower D—Failure to Deal with hypoglycemia;

Upper D—Failure to Deal with hyperglycemia;

E-zone—Erroneous control: X<50 mg/dl and Y>400 mg/dl.

Figure 4:
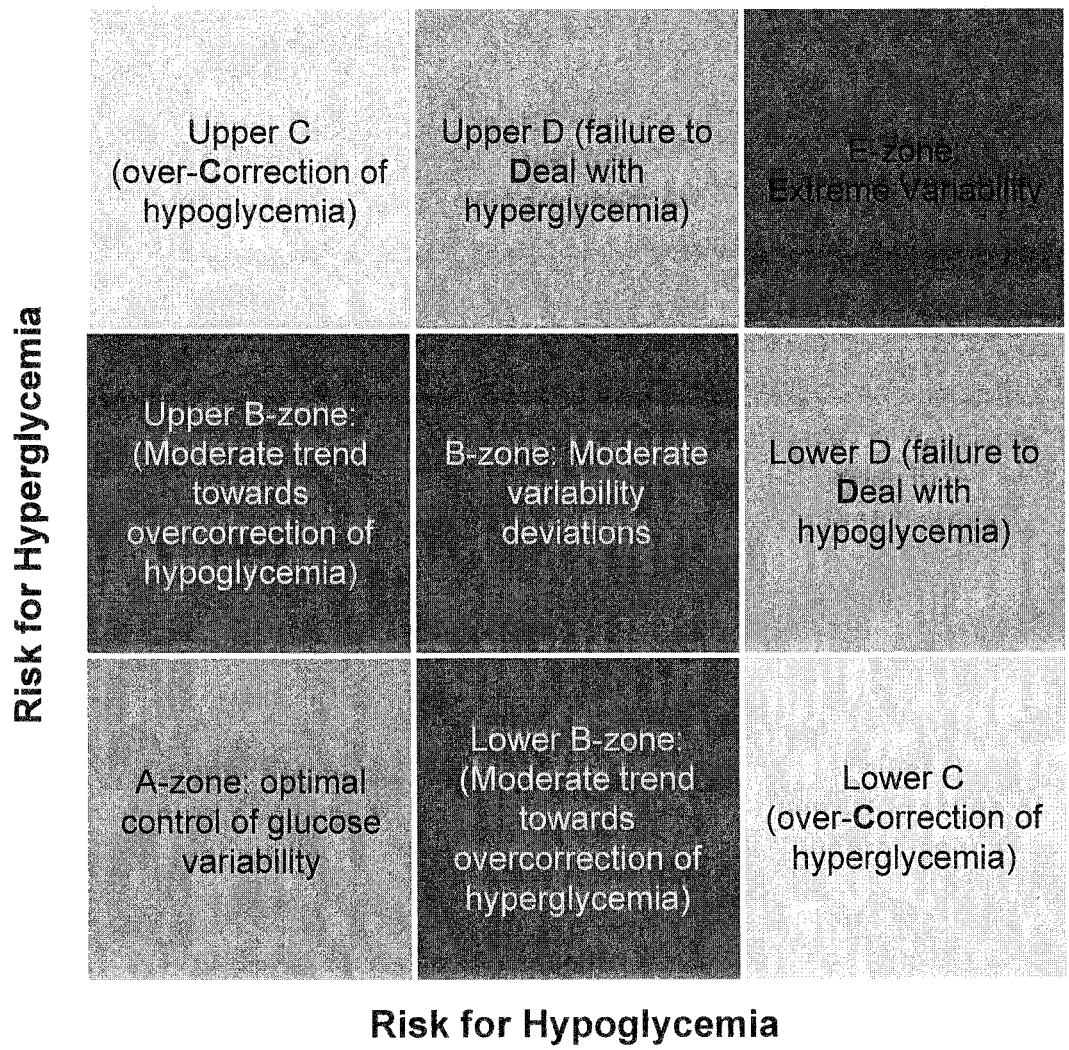
FIG. 4: Provides an embodiment of the aspects of the risk zone (grid) definition of the Variability Grid Analysis (VGA)

FIG. 4 illustrates an aspect of the VGA: The VGA plot area is divided into zones as described above. Each person is represented by one data point for each observation period. For example, with a frequency of 3-4 SMBG readings per day, a reasonable observation period would be one week. In such a case the VGA will present the weekly variability and associated risk for hypo- and hyperglycemia of a person.

The axis of the VGA plot define the type of the plot. Three types are currently suggested:

(1) Min/Max VGA: The 2.5% and the 97.5% of the weekly SMBG and/or CGM data distribution are plotted on the on the X- and Y-axis, respectively. In this case, the difference between Y-X coordinates of the plot would present the weekly range of glucose fluctuations. The scale of the axes is adjusted to encompass the magnitude of the possible minimum and maximum of BG fluctuations: the X-axis ranges from 20 to 110 mg/dl (in reverse order), while the Y-axis ranges from 110 to 600 mg/dl. The Min/Max VGA zones are defined as follows:

A-zone—Optimal control with X-range 110-80 mg/dl and Y-range 110-200 mg/dl;
Lower B—Moderate deviations into hypoglycemia: X=80-50 mg/dl, Y=110-200 mg/dl;
Upper B—Moderate deviations into hyperglycemia: X=110-80 mg/dl, Y=200-400 mg/dl;
B-zone—Moderate deviations with X=80-50 mg/dl and Y=200-400 mg/dl;
Lower C—Over-Correction of hyperglycemia: X<50 mg/dl, Y=110-200 mg/dl;
Upper C—Over-Correction of hypoglycemia: X=110-80 mg/dl, Y>400 mg/dl;
Lower D—Failure to Deal with hypoglycemia: X<50 mg/dl, Y=200-400 mg/dl;
Upper D Failure to Deal with hyperglycemia: X=80-50 mg/dl, Y>400 mg/dl;
E-zone—Extreme variability: X<50 mg/dl and Y>400 mg/dl.

Figure 5:
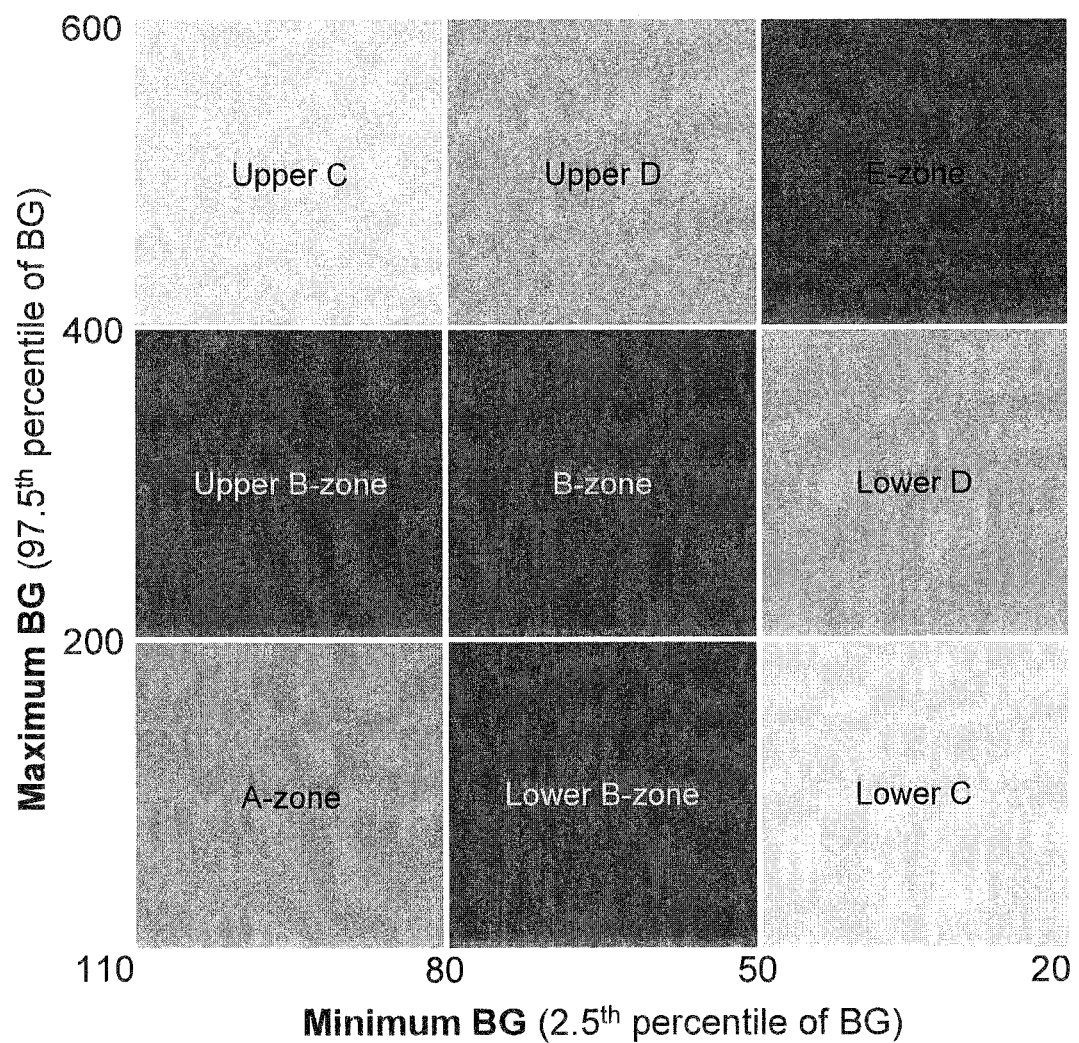
FIG. 5: Provides an embodiment of the aspects of the Min/Max VGA

Other clinically relevant definitions of the Min/Max VGA zones are possible as well. FIG. 5 presents the Min/Max VGA. Points exceeding the limits of the plot are plotted on the outer border.

(2) IQR VGA: The 25% and the 75% of the weekly SMBG and/or CGM data distribution are plotted on the on the X- and Y-axis, respectively. In this case, the difference between Y-X coordinates of the plot would present the weekly Inter-Quartile Range (IQR) of glucose fluctuations. The scale of the axes is adjusted to encompass the magnitude of the possible lower and upper quartiles of the BG fluctuations: the X-axis ranges from 50 to 110 mg/dl (in reverse order), while the Y-axis ranges from 110 to 400 mg/dl. The IQR VGA zones are defined as follows:

A-zone—Optimal control with X-range 110-90 mg/dl and Y-range 110-180 mg/dl;
Lower B—Moderate deviation towards hypoglycemia: X=90-70, Y=110-180 mg/dl;
Upper B—Moderate deviation towards hyperglycemia: X=110-90, Y=180-250 mg/dl;
B-zone—Moderate deviations with X=90-70 mg/dl and Y=180-250 mg/dl;
Lower C—Over-Correction of hyperglycemia: X<70 mg/dl, Y=110-180 mg/dl;
Upper C—Over-Correction of hypoglycemia: X=110-90 mg/dl, Y>250 mg/dl;
Lower D—Failure to Deal with hypoglycemia: X<70 mg/dl, Y=180-250 mg/dl;
Upper D—Failure to Deal with hyperglycemia: X=90-70 mg/dl, Y>250 mg/dl;
E-zone—Extreme variability: X<70 mg/dl and Y>250 mg/dl.

Figure 6:
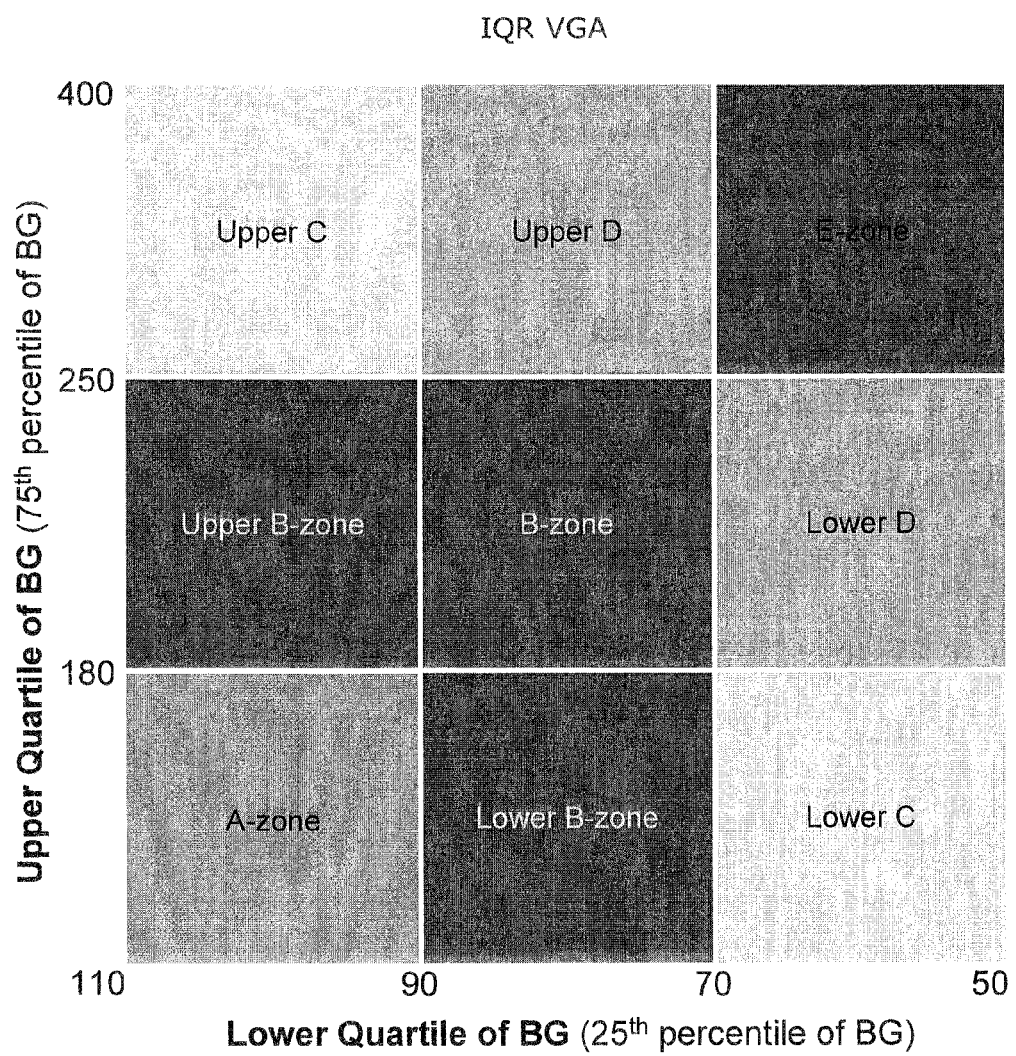
FIG. 6: Provides an embodiment of the aspects of the IQR VGA

Other clinically relevant definitions of the IQR VGA zones are possible as well. FIG. 6 presents the IQR VGA. Points exceeding the limits of the plot are plotted on the border.

(3) Risk VGA: The Low and High BG Indices (LBGI, HBGI, [21]) are plotted on the on the X- and Y-axis, respectively. In this case, the sum of Y-X coordinates of the plot would present the weekly range of glucose risk fluctuations. The boundaries of the Risk VGA zones are determined on the basis of well-established thresholds for the LBGI and HBGI, which have been tested in a number of data sets [26, 27]:

A-zone—Optimal control & low risk with X-range<2.5 and Y-range<5;
Lower B—Moderate deviations towards hypoglycemia: X=2.5-5, Y<5;
Upper B—Moderate deviations towards hyperglycemia: X<2.5, Y=5-10;
B-zone—Moderate deviations with X=2.5-5 and Y=5-10;
Lower C—Over-Correction of hyperglycemia: X>5, Y<5;
Upper C—Over-Correction of hypoglycemia: X<2.5, Y>10;
Lower D—Failure to Deal with hypoglycemia: X>5, Y=5-10;
Upper D—Failure to Deal with hyperglycemia: X=2.5-5, Y>10;
E-zone—Extreme variability: X>5 and Y>10.

Figure 7:
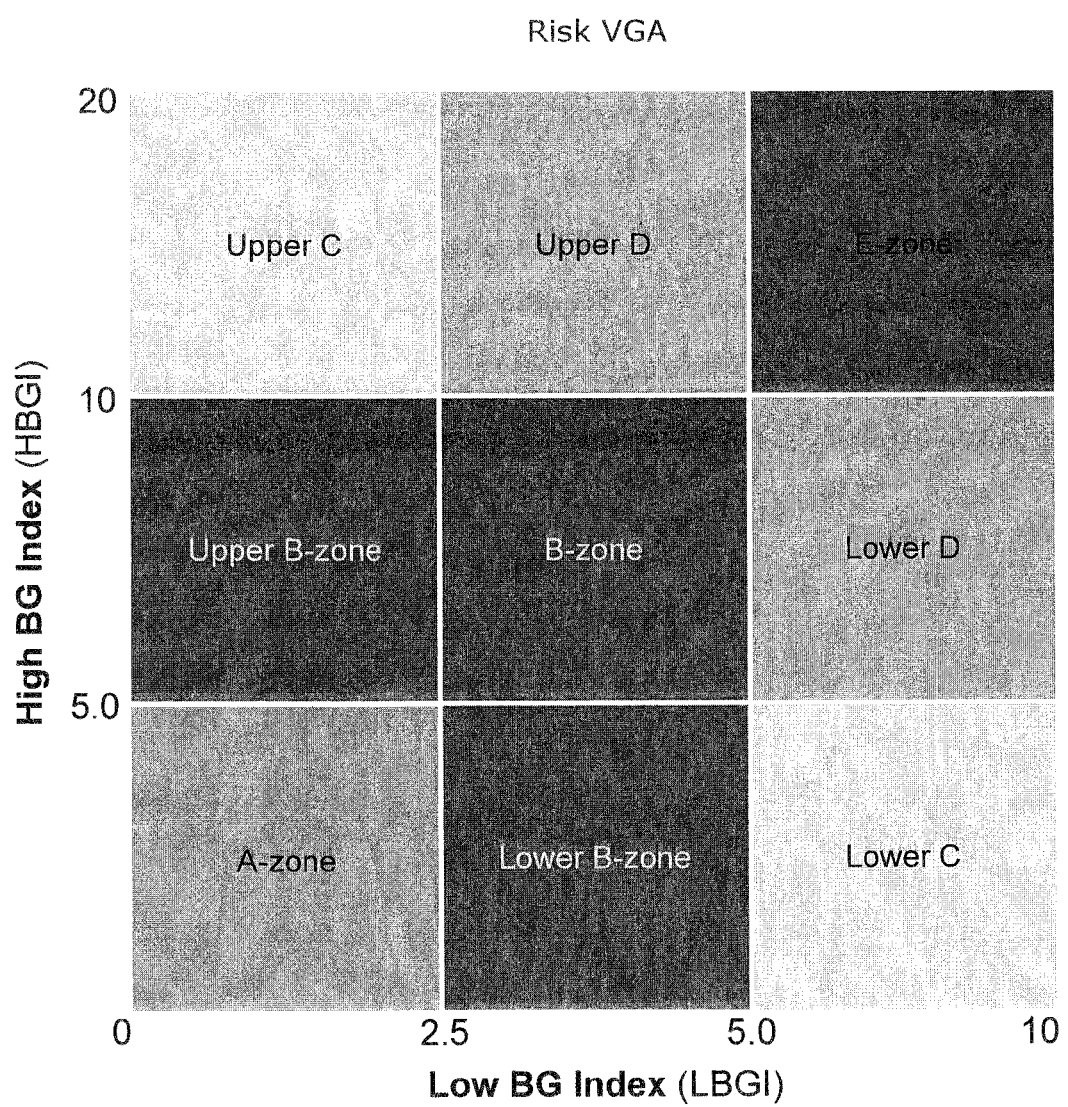
FIG. 7: Provides an embodiment of the aspects of the Risk VGA

The axes here represent risk units related to BG via a nonlinear transformation [18]. Other clinically relevant definitions of the Risk VGA zones are possible as well. FIG. 7 presents the Risk VGA. Points exceeding the limits of the plot are plotted on the border.

Theoretical Mathematical Base:

Min/Max and IQR VGA: The BG levels are measured in mg/dl in the USA and in mmol/L most elsewhere. The two scales are directly related by 18 mg/dl=1 mmol/l. The measuring range of most BG meters is 20 to 600 mg/dl, which is considered to cover practically all observed values. The target BG range for a person with diabetes is considered to be 70 to 180 mg/dl. Hypoglycemia is identified as a BG below 70 mg/dl, hyperglycemia is a BG above 180 mg/dl. These ranges explain the boundaries and cutoff values of the Min/Max VGA and the IQR VGA (FIGS. 5 and 6, respectively).

Risk VGA: To explain the Risk VGA we refer to our previously introduced theory of Risk Analysis of BG data [21, 26, 27]. In brief, the BG measurement scale is numerically asymmetric—the hyperglycemic range (180 to 600 mg/dl) is much greater that the hypoglycemic range (20-70 mg/dl) and the euglycemic range (70-180 mg/dl) is not centered within the scale. We have corrected this asymmetry by introducing a transformation f(BG)—a continuous function defined on the BG range [20, 600] that has the general two-parameter analytical form [18]:

$$f(BG, \alpha, \beta) = [(\ln(BG))^\alpha - \beta], \; \alpha, \beta > 0$$

and satisfies the assumptions:
A1: $f(600, \alpha, \beta) = -f(20, \alpha, \beta)$ and
A2: $f(180, \alpha, \beta) = -f(70, \alpha, \beta)$.

By multiplying by a third parameter $\gamma$ we fix the minimal and maximal values of the transformed BG range at $-\sqrt{10}$ and $\sqrt{10}$ respectively. When solved numerically under the restriction $\alpha > 0$, these equations give: $\alpha = 1.084$, $\beta = 5.381$, $\gamma = 1.509$. These parameters are sample-independent and have been fixed in 1997 [18].

After fixing the parameters of f(BG) depending on the measurement scale that is being used, we define the quadratic function $r(BG) = 10 \cdot f(BG)^2$, which defines the BG Risk Space. The function r(BG) ranges from 0 to 100. Its minimum value is 0 and is achieved at BG=112.5 mg/dl, a safe euglycemic BG reading, while its maximum is reached at the extreme ends of the BG scale 20 mg/dl and 600 mg/dl. Thus, r(BG) can be interpreted as a measure of the risk associated with a certain BG level. The left branch of this parabola identifies the risk of hypoglycemia, while the right branch identifies the risk of hyperglycemia. These branches are identified by the formulas [18]:

$$rl(BG)=r(BG) \text{ if } f(BG)<0 \text{ and } 0 \text{ otherwise (left branch);} \quad (1)$$

$$rh(BG)=r(BG) \text{ if } f(BG)>0 \text{ and } 0 \text{ otherwise (right branch).} \quad (2)$$

The conversion of BG values into associated risk values serves as a base of the Risk VGA presented in FIG. 7. The X-axis represents risk for hypoglycemia, while the Y-axis represents the risk for hyperglycemia. The cutoff risk points have been identified in previous studies [21,23,27].

Tracing Glucose Fluctuations Over Time: All VGA analyses allow tracing a single person or a population over time. In order to do so, we predefine a sequence of time periods, which serve as basic time units for the analyses. With a frequency of 3-4 SMBG readings per day, a reasonable time period is a week, which would allow 20-30 SMBG readings to be accumulated for the computation of dependable VGA statistics. One point in any of the VGA graphs represents the data of one subject for one period of time. This representation leads to a theoretical paradigm—the theory of Markov Chains [29]—which is frequently used to describe the evolution of a population of individuals over time. In our case, we will use discrete Markov chains with finite state space to describe the transitions of a subject and the population across the zones of the VGA over time. This approach will give us the theoretical tools to estimate: (i) the probabilities of the "average" person's transition from one zone of the VGA to another in one or more time periods, and (ii) the shifts in population distribution across the VGA zones due to various treatments.

In brief, a Markov chain is a stochastic process with discrete state space and discrete time, which has the Markov property (named after the Russian mathematician Andrey Markov 1856-1922). Having the Markov property means that, given the present state, future states are independent of the past states. In other words, the description of the present state fully captures all the information that could influence the future evolution of the process. In the case of VGA this is a reasonable assumption as the time periods are sufficiently long (e.g. a week) to encompass the parameters of diabetes management that are important for the next week. Mathematically, the Markov Property is written as:

$$P(X_\perp(t+1)=x|X_\perp t=x_\perp t, X_\perp(t-1)=x_\perp(t-1), \ldots, X_\perp 1=x_\perp 1)=P(X_\perp(t-1)=x|X_\perp t=x_\perp t)$$

The evolution of a Markov chain is therefore entirely controlled by its matrix of transition probabilities from one step to the next:

$$P_\perp ij(t)=P(X_\perp t=j|X_\perp(t-1)=i) \quad (3)$$

If this matrix does not depend on time (t) then the Markov chain is stationary. For the purposes of VGA we cannot assume that the Markov chain describing the progression of the population would be stationary. On the contrary, changes in its transition probabilities would reflect the effects of treatment.

The state space of the VGA Markov chain has 9 elements and is the set of VGA zones:

{A, Lower_B, Upper_B, B, Lower_C, Upper_C, Lower_D, Upper_D, E}

For practical applications, the state space can be reduced to fewer elements depending on the clinical question in hand. For example, if the clinical question is whether one treatment is better than other in terms of less significant treatment deviations occurring, A and B-zones can be combined and C-, D- and E-zones can be combined as well to yield a binary state space {A+B, C+D+E} identifying the two possibilities of acceptable vs. unacceptable glucose variability resulting from treatment.

Data Retrieval:

Let for each subject (k), k=1, 2, ..., N:

$X_{k1}^1, X_{k2}^1, \ldots X_{kn}^1$ be a series of $n_k^1$ SMBG and/or CGM readings taken during time period 1;

$X_{k1}^2, X_{k2}^2, \ldots X_{kn}^2$ be a series of $n_k^2$ SMBG and/or CGM readings taken during time period 2;

...

$X_{k1}^M, X_{k2}^M, \ldots X_{kn}^M$ be a series of $n_k^M$ SMBG and/or CUM readings taken during time period M;

Where the number of time periods of observation is M≥1 (M=1 would mean that a VGA snapshot of the population is presented, with each individual represented by a single data point). Here we would also require a certain amount of SMBG and/or CGM readings to be accumulated per person per time period (a week) for a data point to be included in the VGA. For example, we can require $n_k^1, n_k^2, \ldots x_k^M \geq 10$ for any subject (k). This does not mean that all subjects should be represented in all time periods. If a subject during a time period does not accumulate at least 10 data points, this time period is simply skipped for that subject.

Computing the Coordinates of Each Data Point in the Min/Max VGA and the IQR VGA:

First, sort the readings $x_{k1}^t, x_{k2}^t, \ldots x_{kn}^t$ of each subject (k) and for each time period (t) in ascending order $x_{k(1)}^t < x_{k(2)}^t < \ldots < x_{k(n)}^t$:

For Min/Max VGA find the 2.5$^{th}$ and 97.5$^{th}$ percentile in the sequence $x_{k(1)}^t < x_{k(2)}^t < \ldots < x_{k(n)}^t$ and assign the X-coordinate of the data point at the 2.5$^{th}$ percentile and the Y-coordinate of the data point at the 97.5$^{th}$ percentile, the difference between the two coordinates Y-X will then be an estimate of the 95% confidence interval for the data of subject (k) and for time period (t).

For IQR VGA find the 25th and 75th percentile in the sequence $x_{k(1)}^t < x_{k(2)}^t < \ldots < x_{k(n)}^t$ and assign the X-coordinate of the data point at the 25$^{th}$ percentile and the Y-coordinate of the data point at the 75$^{th}$ percentile. The difference between the two coordinates Y-X will then be the inter-quartile range for the data of subject (k) and for time period (t).

Computing the Coordinates of Each Data Point in the Risk VGA:

In this case, sorting of the SMBG and/or CGM readings is not needed. The first step of analysis is to transform the readings $x_{k1}^t < x_{k2}^t < \ldots < x_{kn}^t$ of each subject (k) and for each time period (t) into their corresponding low- and high-risk values $rl(x_{ks}^t)$ and $rh(x_{ks}^t)$ using formulas (a) and (2) introduced in the previous subsection.

The Low and High BG indices for subject (k) and for each time period (t) are then computed as the averages:

$$LBGI_k^t = \frac{1}{n_k^t} \sum_{s=1}^{n_k^t} rl(x_{ks}^t) \text{ and } HBGI_k^t = \frac{1}{n_k^t} \sum_{s=1}^{n_k^t} rh(x_{ks}^t)$$

The X-coordinate of a data point representing subject (k) in time period (t) is $X=LBGI_k^t$. The Y-coordinate of a data point representing subject (k) in time period (t) is $Y=HBGI_k^t$. The sum of the coordinates X+Y is equal to the previously introduced BG Risk Index—a measure of the total variance of BG fluctuations in risk space [21].

Output Measures of the VGA:

Percentage within VGA Zones:

For all three analyses—Min/Max, IQR, and Risk VGA—the most straightforward interpretation or the plot uses the percentage of data points within each VGA zone. The percentage distribution across the VGA zones indicates the degree of glucose variability and the degree of treatment deviations towards hypo- or hyperglycemia observed in a population. This computation can be implemented in any statistical package or other software using the following statements:

Min/Max VGA: The X-Y coordinates of each data point of the Min/Max VGA are sent through the sequence of commands below. The output variable is ZONE, coded as:
ZONE=1 for A-zone;
ZONE=2 for Lower B;
ZONE=3 for Upper B;
ZONE=4 for B-zone;
ZONE=5 for Lower C;
ZONE=6 for Upper C;
ZONE=7 for Lower D;
ZONE=8 for Upper D;
ZONE=9 for E-zone;

Essentially, with the progression of a person through time the variable ZONE will move through some or all of the states of the Markov chain introduced in Section E.2.

This means that one person will be one "realization" or trajectory in this stochastic process.
ZONE=0
If (X>=80) and (Y<=200) ZONE=1
If (X>=50 and X<80) and (Y<=200) ZONE=2
If (X>=80) and (Y>200 and Y<=400) ZONE=3
If (X>=50 and X<80) and (Y>200 and Y<=400) ZONE=4
If (X<50) and (Y<200) ZONE=5
If (X>=80) and (Y>400) ZONE=6
If (X<50) and (Y>200 and Y<=400) ZONE=7
If (X>=50 and X<80) and (Y>400) ZONE=8
If (X<50) and (Y>400) ZONE=9

IQR VGA: The X-Y coordinates of each data point of the IQR VGA are sent through the sequence of commands below. The output variable is ZONE, coded as with Min/Max VGA:
ZONE=0
If (X>=90) and (Y<=180) ZONE=1
If (X>=70 and X<90) and (Y<=180) ZONE=2
If (X>=90) and (Y>180 and Y<=250) ZONE=3
If (X>=70 and X<90) and (Y>180 and Y<=250) ZONE=4
If (X<70) and (Y<180) ZONE=5
If (X>=90) and (Y>250) ZONE=6
If (X<70) and (Y>180 and Y<=250) ZONE=7
If (X>=70 and X<90) and (Y>250) ZONE=8
If (X<70) and (Y>250) ZONE=9

Risk VGA: The X-Y coordinates of each data point of the Risk VGA are sent through the sequence of commands below. The output variable is ZONE, coded as with Min/Max VGA:
ZONE=0
If (X<=2.5) and (Y<=5) ZONE=1
If (X>2.5 and X<=5) and (Y<=5) ZONE=2
If (X<=2.5) and (Y>5 and Y<=10) ZONE=3
If (X>2.5 and X<=5) and (Y>5 and Y<=10) ZONE=4
If (X>5) and (Y<5) ZONE=5
If (X<=2.5) and (Y>10) ZONE=6
If (X>5) and (Y>5 and Y<=10) ZONE=7
If (X>2.5 and X<=5) and (Y>10) ZONE=8
If (X>5) and (Y>10) ZONE=9

Transition Probabilities and Stationary Distribution:

As the observed population progresses through the zones of the VGA (any variant) the transition probabilities defined by formula (3) are estimated during the shift from one observation period to the next. The estimation includes counting the number of people who changed their state from (i) to (j) or remained in state (i), i,j=1, 2, ..., 9 during the transition from time period t-1 to time period t. For any subject (k) we define:

$P_{ij}^k(t)=1$ if $P(K_\perp t=j|K_\perp(t-1)=i)$ and 0 otherwise

In other words, if the subject was at state (i) at step n−1 ($K_{t-1}$=i) and then moved to state (j) then the transition $P_{ij}^k$=1; otherwise $P_{ij}^k$=0. Here, we don't exclude the possibility i=j, which means that the subject remains in the same state of the VGA. The transition probability matrix of the Markov chain describing the VGA is then estimated as the average of $P_{ij}^k$ across all subjects:

$$P_{ij}(t) = \frac{1}{N}\sum_{k=1}^{N} p_{ij}^k(t)$$

for any i,j=1, 2, ..., 9

If the subject population is stationary, i.e. not undergoing active treatment, then the transition probability matrix would not depend on the time (t).

The stationary distribution of the Markov chain will be representative of the "steady state" of the distribution of the subjects across the VGA zones. In the case of stationary Markov chain (no active treatment) the stationary distribution should be close to the percentage distributions across the VGA zones presented in the previous section for each variant of the VGA. If the process is not stationary, i.e., the subjects are undergoing active treatment, the stationary distribution of the Markov chain will indicate what would be the distribution of subjects across the VGA zones if the current state of the treatment is sustained.

The stationary distribution $\sigma_i$, i=1, 2, ... 9 is computed from the transition probability matrix by solving the system of equations:

$$\sigma_i = \sum_{j=1}^{g} p_{ij}(n) \cdot \sigma_j$$

for any i=1, 2, ..., 9

In other words, the stationary distribution of the Markov chain describing the VGA is the left eigenvector of its transition probability matrix. The Markov chain interpretation and the computation of transition probabilities and stationary distribution is the same for all three variants of the VGA—Min/max; IQR, and Risk VGA. The difference in the results will come from the different definitions of the VGA zones specific to each variant of the analysis.

Validation of the VGA

We validate the VGA by comparing its results to established numerical method for measuring glucose variability and risk for hypo- and hyperglycemia—the Average Daily Risk Range (ADRR) [25]. Specifically, we use a large data set containing data for N=335 people with T1DM or T2DM (mean HbA1c=7.9, each followed for 4 months with SMBG) to plot the Min/max; IQR, and Risk VGA in each of the four risk categories of the ADRR: Low Risk: ADRR<20; Moderate Risk: 20<=ADRR<40, and High Risk: ADRR>40 [25].

Tables of the distribution of the VGA zones across the risk categories defined by the ADRR are included as well showing the compatibility of the visual output of the VGA with the numerical estimates of glucose variability provided by the ADRR. The VGA plots include the first 4 weeks of observation. Each person is represented by one data point.

Figure 8A:
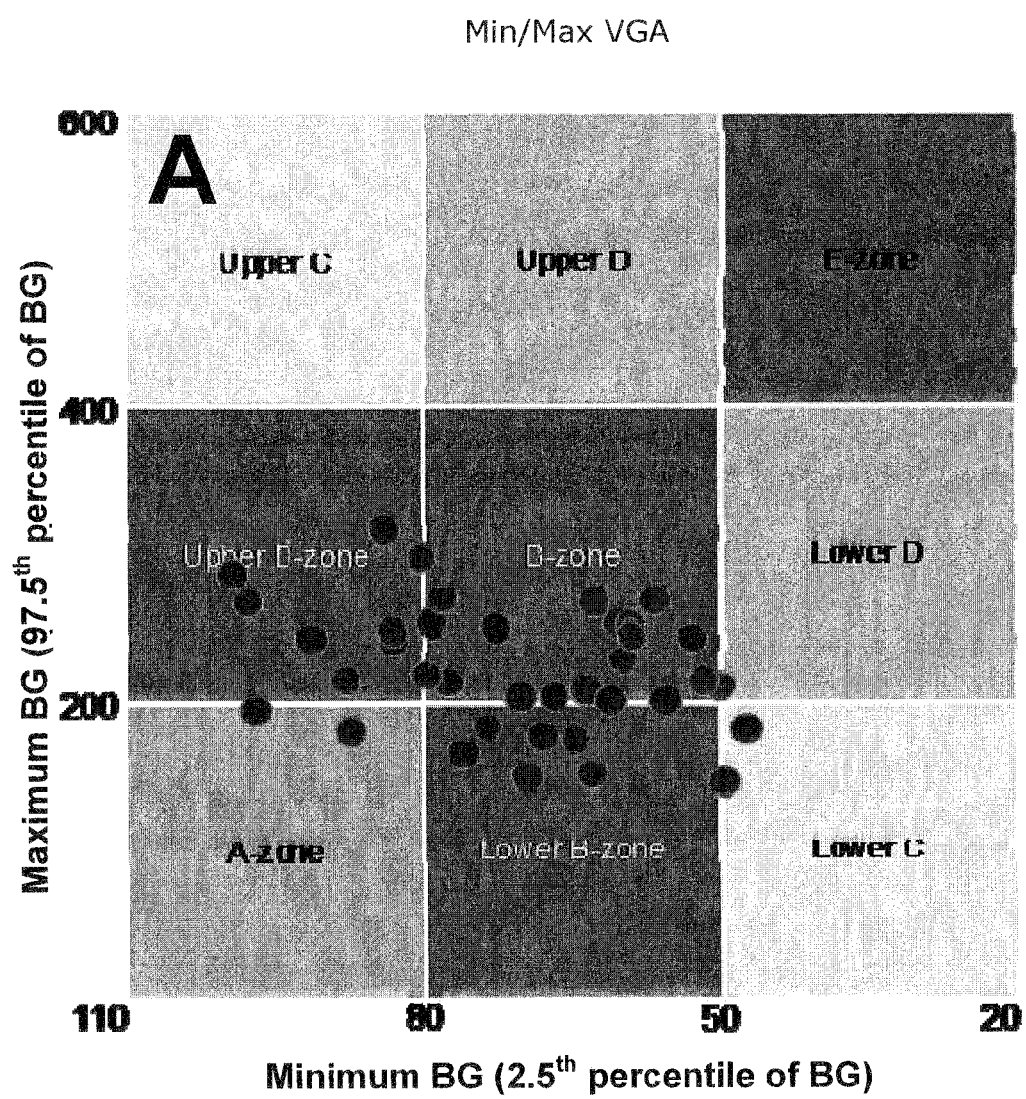
FIG. 8: Provides an illustration of the Min/Max VGA presenting subjects in the three risk categories defined by the ADRR: Low, Moderate, and High risk corresponding to FIGS. 8(A), (B), (C), respectively.
Figure 8B:
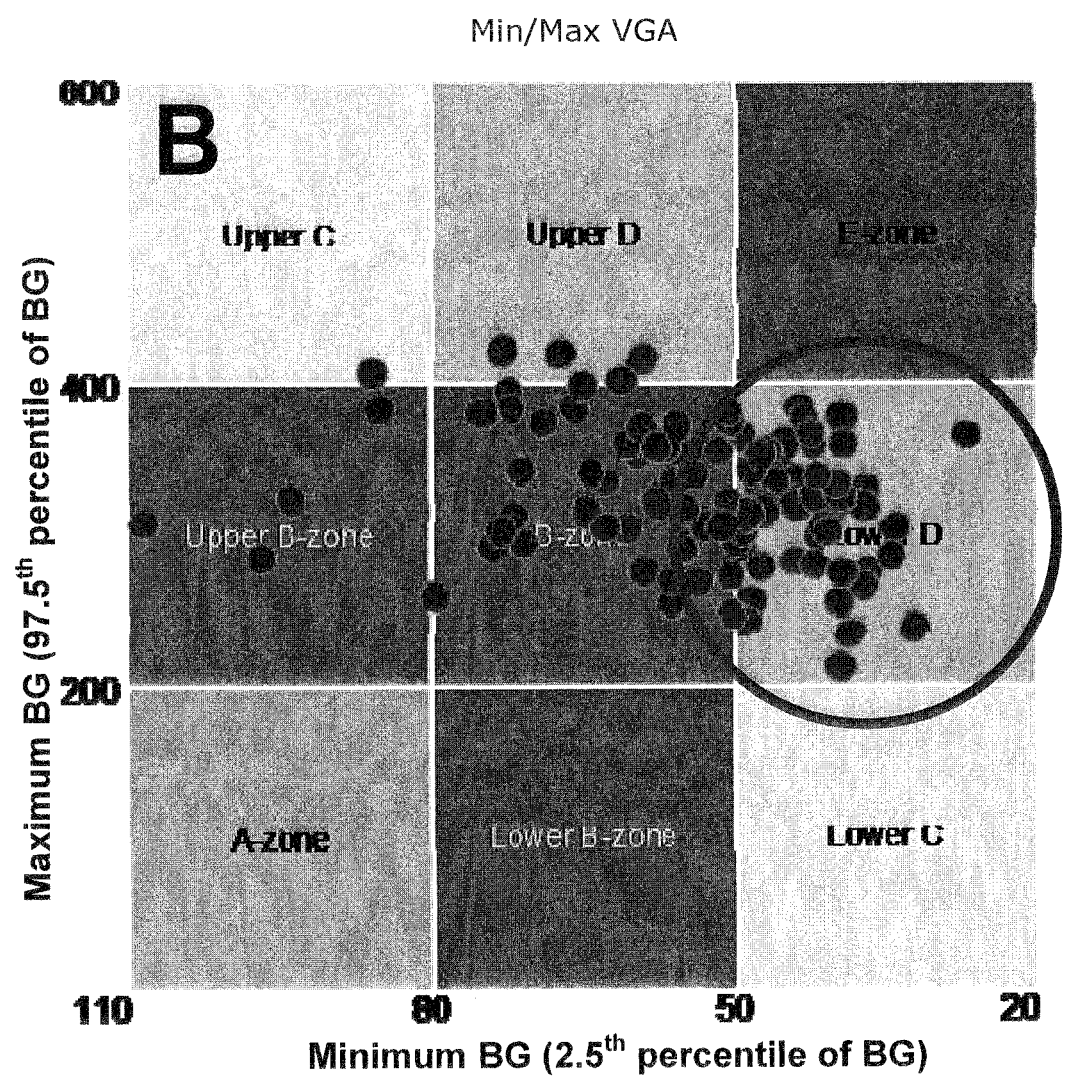
Figure 8C:
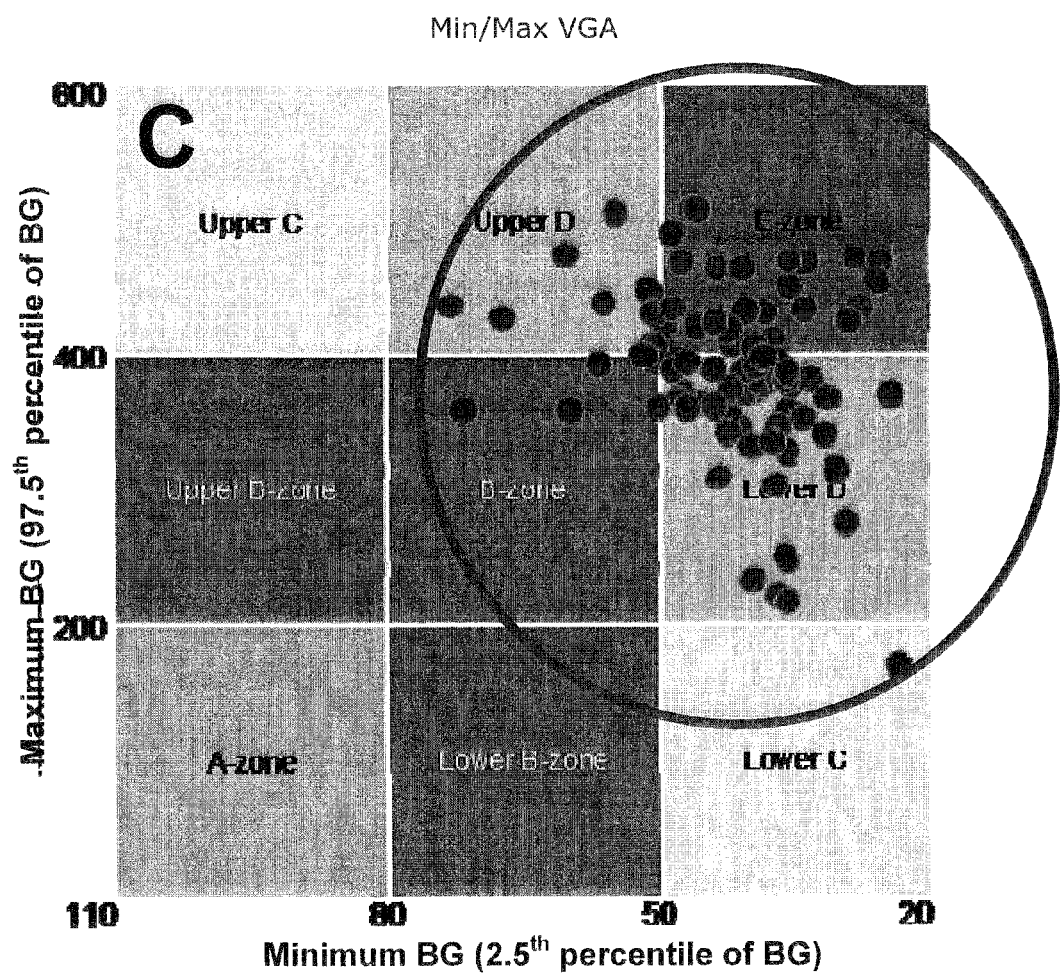

FIG. 8 presents an embodiment of an aspect of the Min/Max VGA of subjects in the three risk categories defined by the ADRR: Low, Moderate, and High risk corresponding to FIGS. 8(A), (B), (C), respectively. It is evident that the distribution of extremes shifted progressively to unfavorable upper and lower zones for people at moderate and high risk. This is reflected by the percent readings in each of the VGA zones presented in Table 1 below:

TABLE 1

Min/Max VGA Distribution in Relationship with the ADRR

| Zone | ADDR < 20 | 20 <= ADDR < 40 | ADDR > 40 |
|---|---|---|---|
| A | 5.4% | 0% | 0% |
| B = Lower + Upper + B | 86.5% | 47.0% | 4.5% |
| C = Lower + Upper | 5.4% | 2.6% | 5.6% |
| D = Lower + Upper | 2.7% | 50.4% | 60.7% |
| E | 0% | 0% | 29.2% |

Figure 9A:
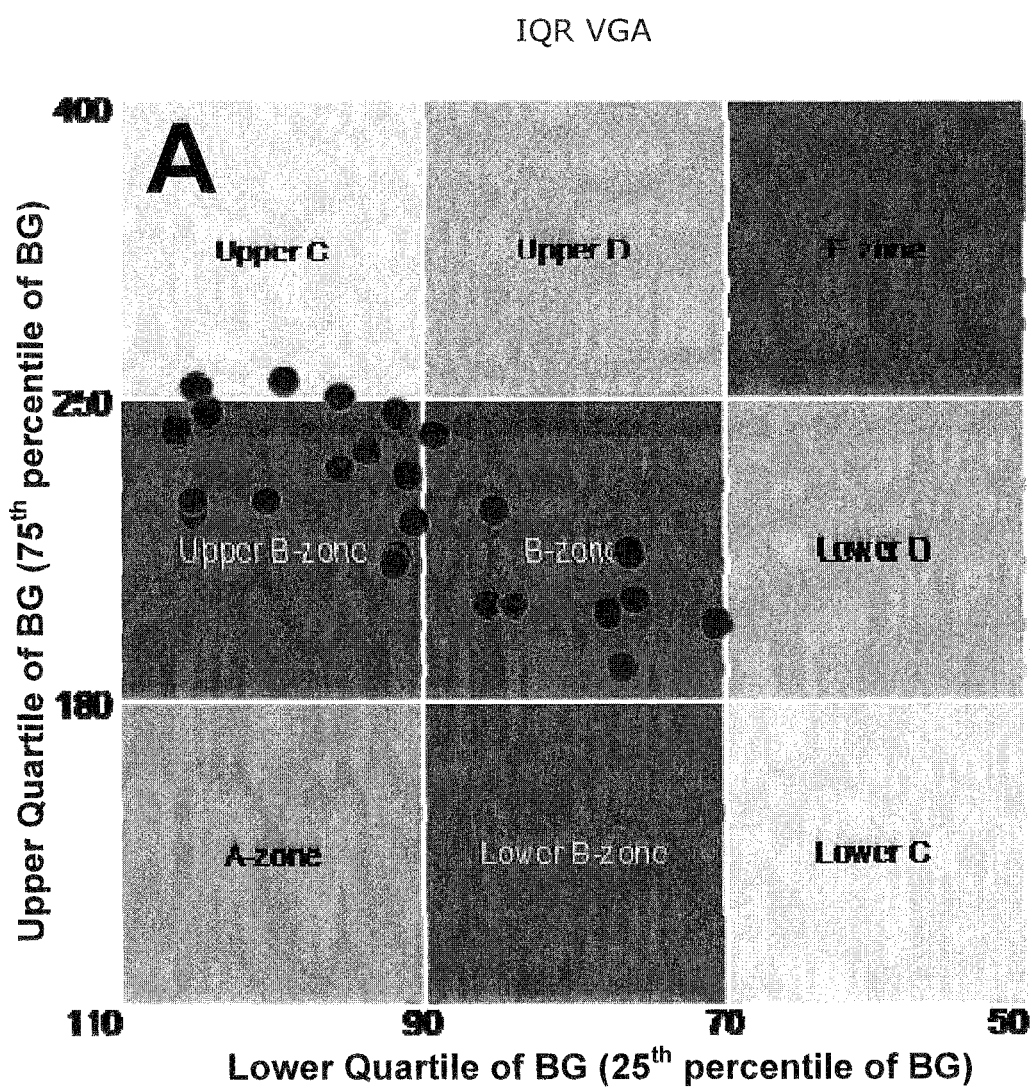
FIG. 9: Provides an illustration of the IQR VGA presenting subjects in the three risk categories defined by the ADRR: Low, Moderate, and High risk corresponding to FIGS. 9(A), (B), (C), respectively.
Figure 9B:
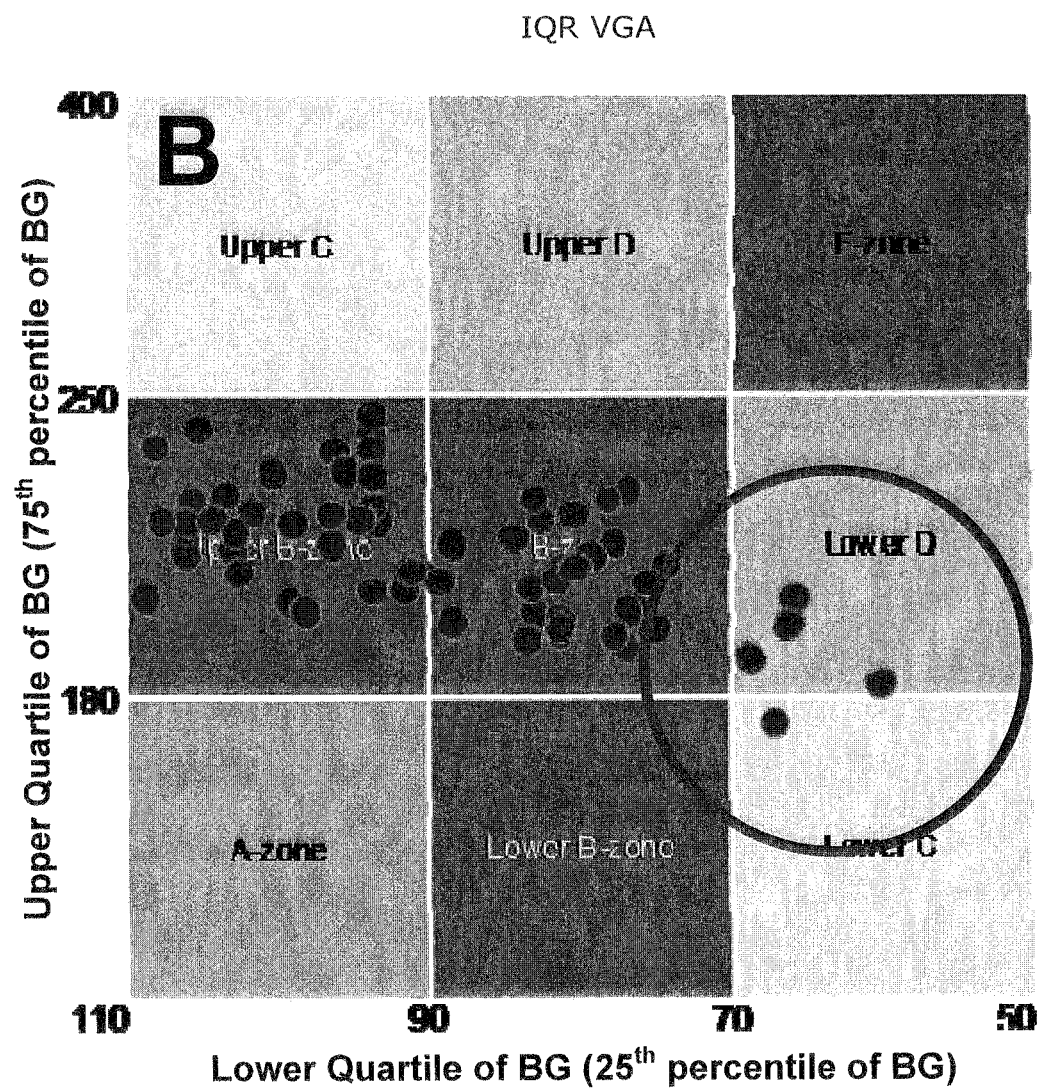
Figure 9C:
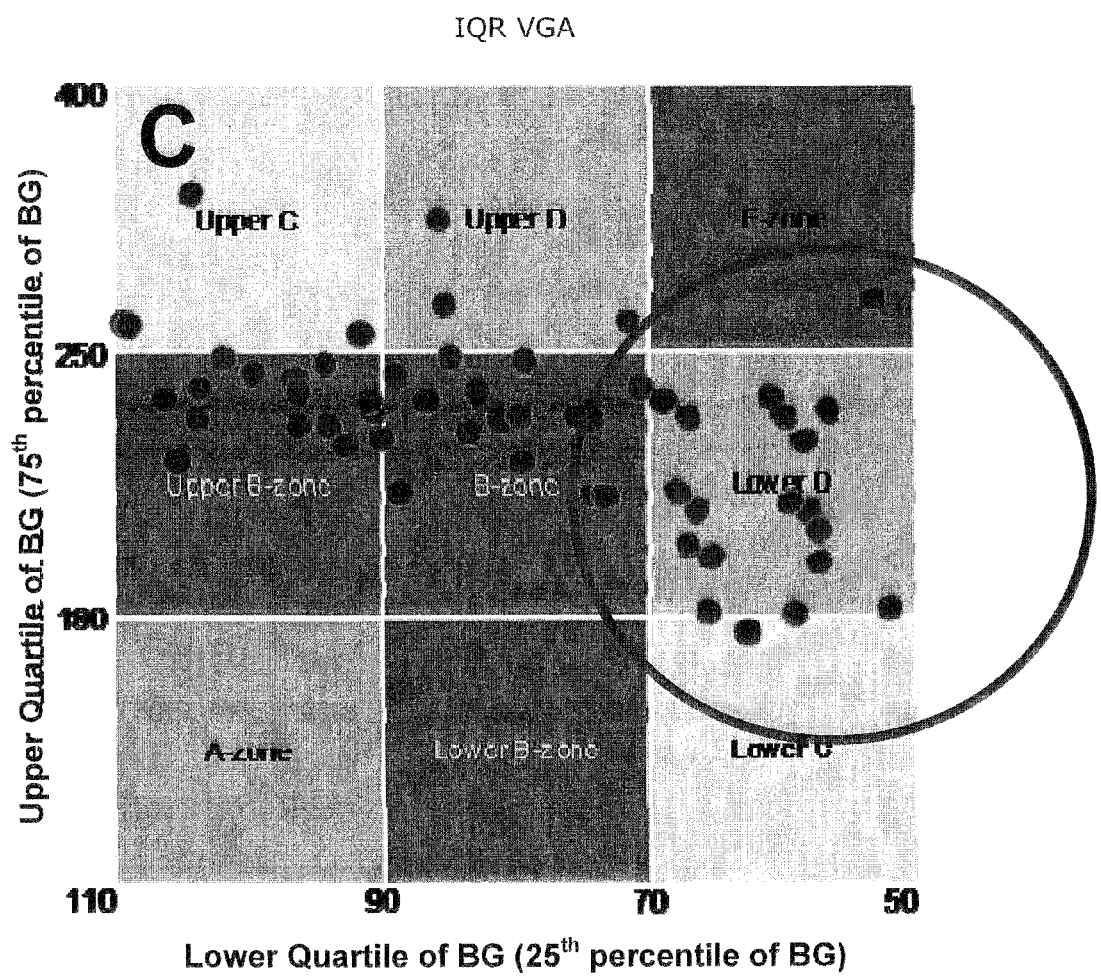

FIG. 9 presents an embodiment of an aspect of the IQR VGA of subjects in the three risk categories defined by the ADRR: Low, Moderate, and High risk corresponding to FIGS. 9(A), (B), (C), respectively. It is evident that the distribution of extremes shifted progressively to unfavorable upper and lower zones for people at moderate and high risk. This is reflected by the percent readings in each of the VGA zones presented in Table 2 below:

TABLE 2

IQR VGA Distribution in Relationship with the ADRR

| Zone | ADDR < 20 | 20 <= ADDR < 40 | ADDR > 40 |
|---|---|---|---|
| A | 59.5% | 3.5% | 0% |
| B = Lower + Upper + B | 40.5% | 80.0% | 29.2% |
| C = Lower + Upper | 0% | 16.5% | 51.7% |
| D = Lower + Upper | 0% | 0% | 18.0% |
| E | 0% | 0% | 1.1% |

Figure 10A:
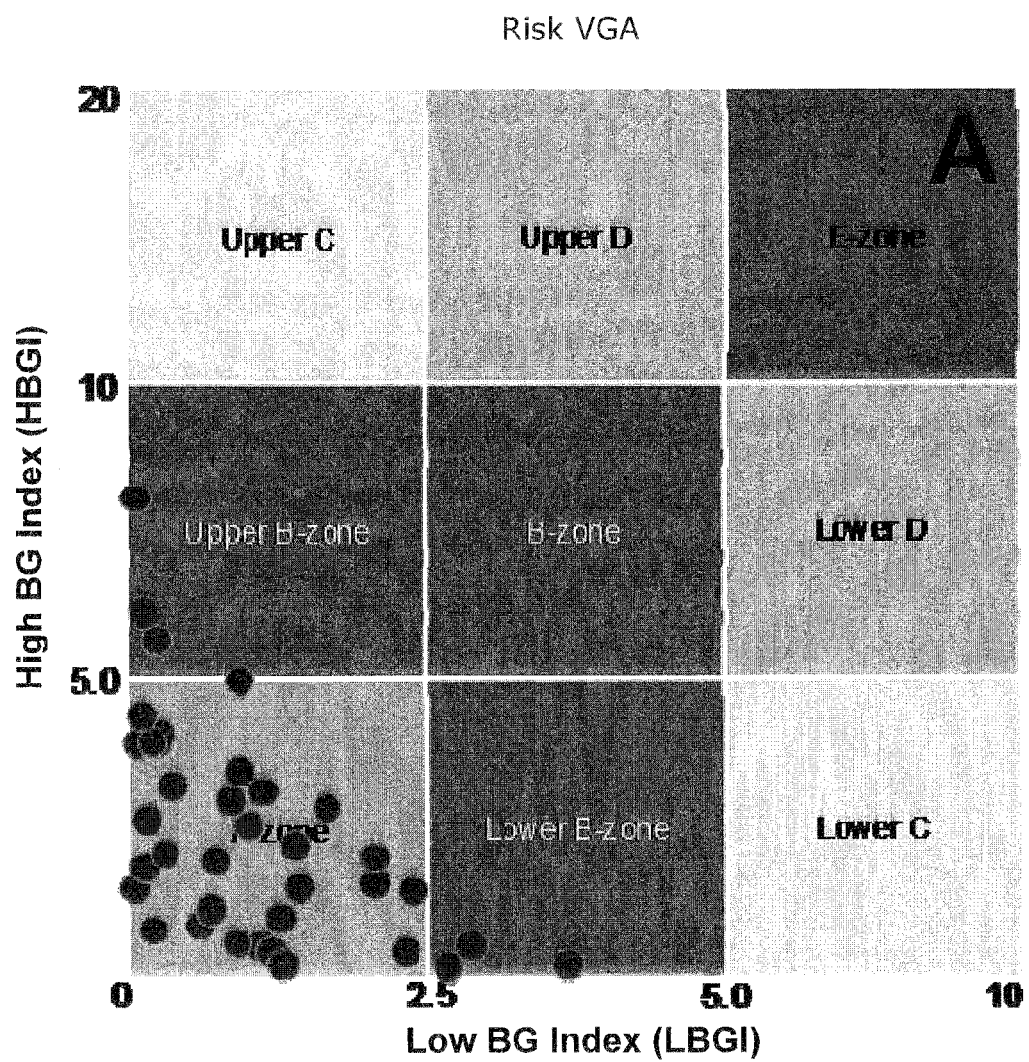
FIG. 10: Provides an illustration of the Risk VGA of subjects in the three risk categories defined by the ADRR: Low, Moderate, and High risk corresponding to FIGS. 10(A), (B), (C), respectively.
Figure 10B:
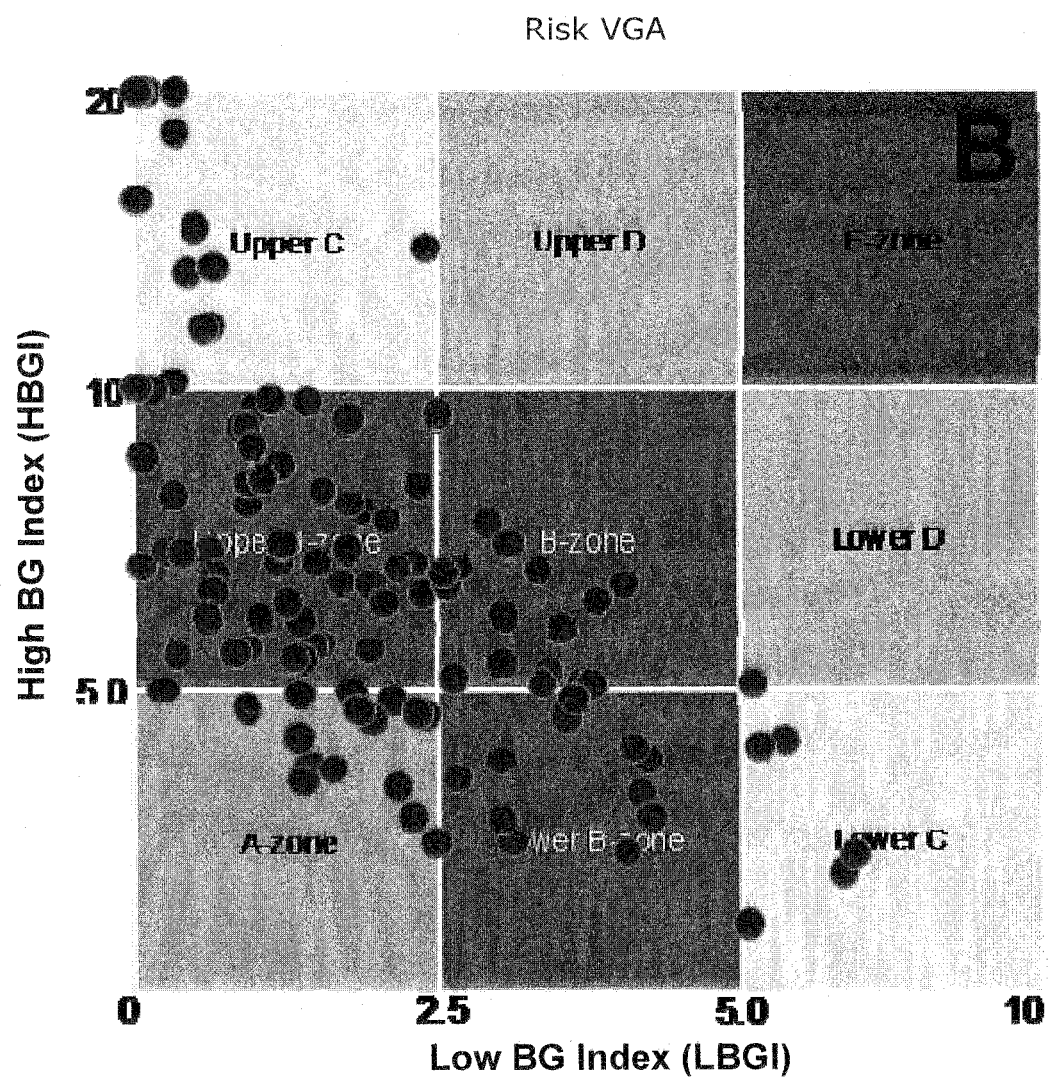
Figure 10C:
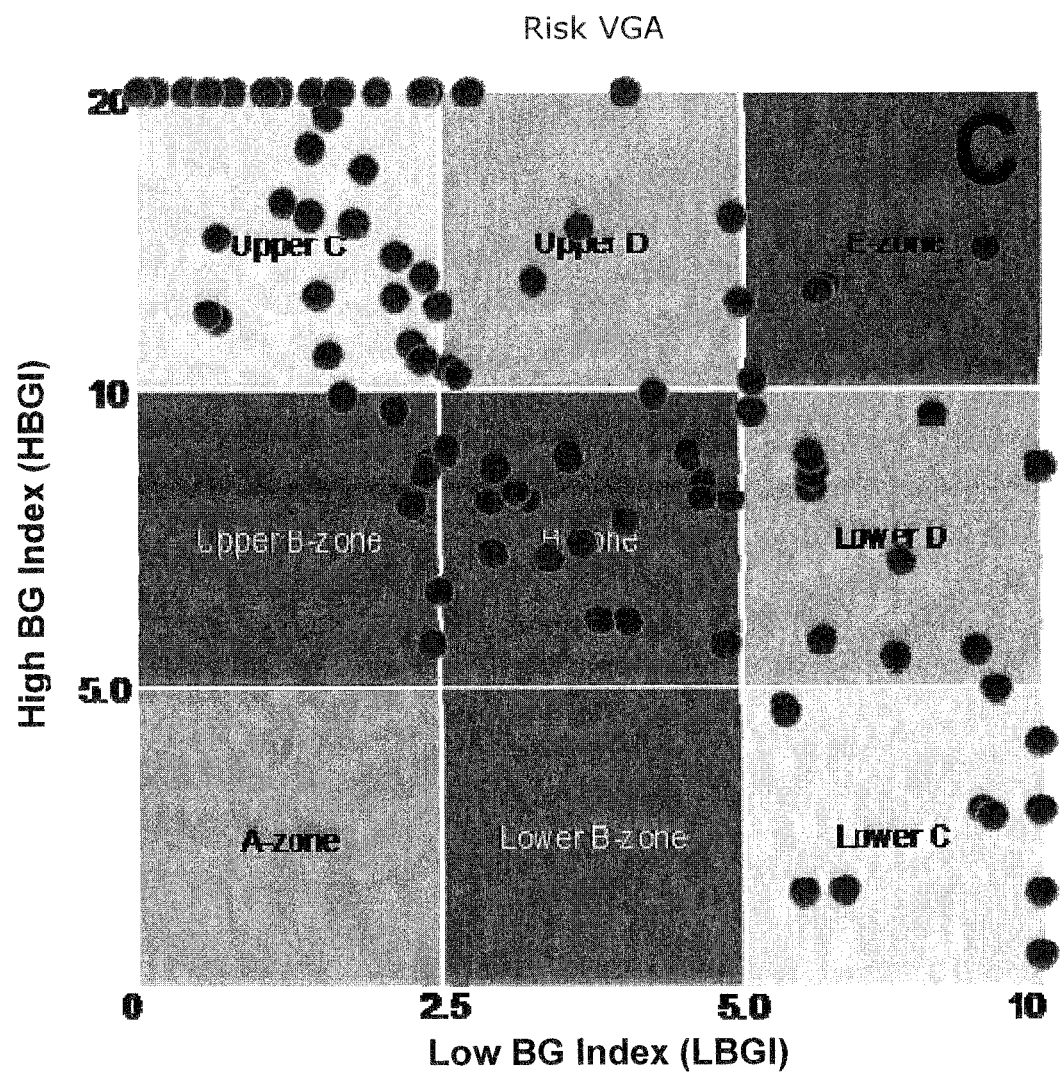

FIG. 10 presents an embodiment of an aspect of the Risk VGA of subjects in the three risk categories defined by the ADRR: Low, Moderate, and High risk corresponding to FIGS. 10(A), (B), (C), respectively. It is evident that the distribution of extremes shifted progressively to unfavorable upper and lower zones for people at moderate and high risk. This is reflected by the percent readings in each of the VGA zones presented in Table 3 below:

TABLE 3

Risk VGA Distribution in Relationship with the ADRR

| Zone | ADDR < 20 | 20 <= ADDR < 40 | ADDR > 40 |
|---|---|---|---|
| A | 56.8% | 2.6% | 0% |
| B = Lower + Upper + B | 40.5% | 53.0% | 5.6% |
| C = Lower + Upper | 2.7% | 31.3% | 34.8% |
| D = Lower + Upper | 0% | 13.0% | 39.3% |
| E | 0% | 0% | 20.2% |

Figure 15A:
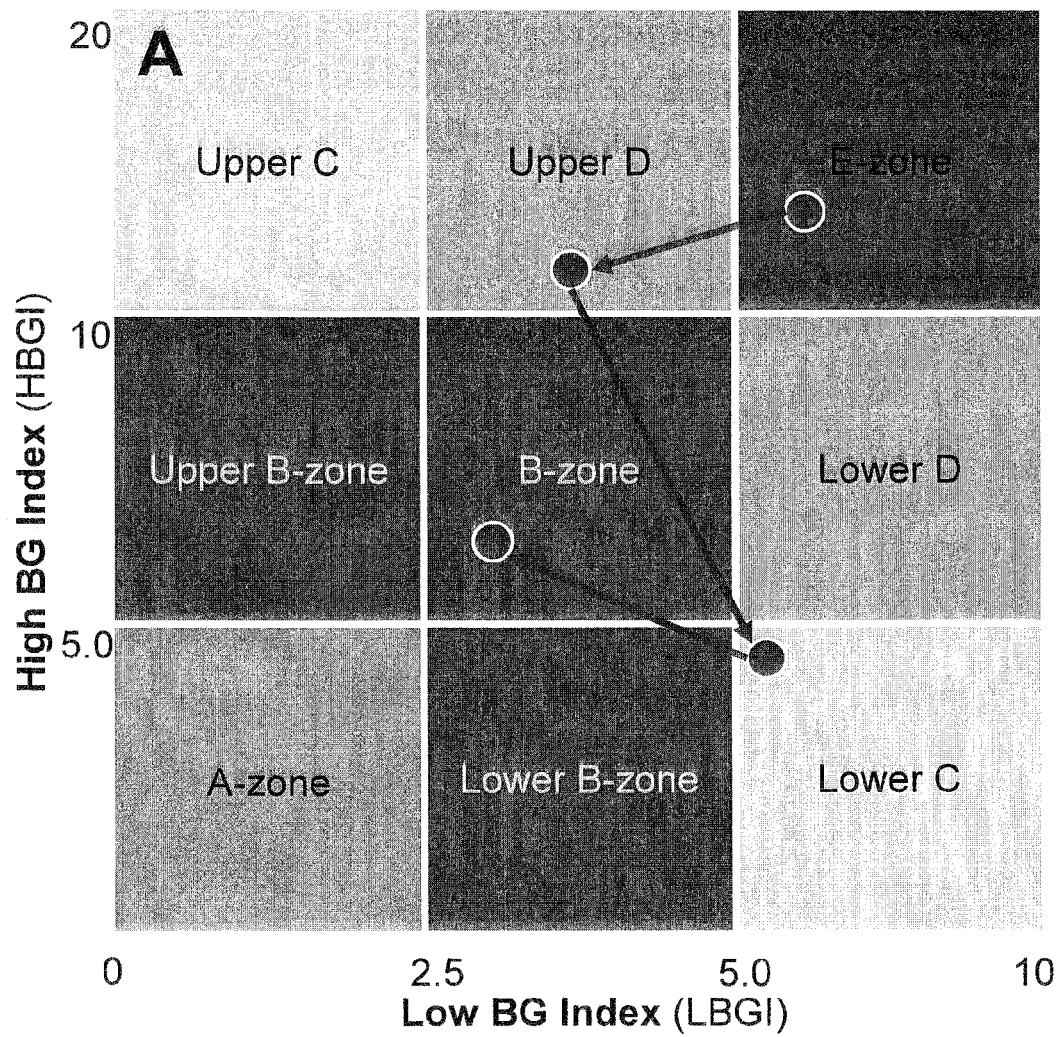
FIG. 15: Provides an aspect of an embodiment of the present invention for tracking the progress of a single person over 4 months using Risk VGA for 1) gradual improvement of glucose variability; and 2) gradual deterioration of glucose variability for FIGS. 15(A) and (B), respectively.
Figure 15B:
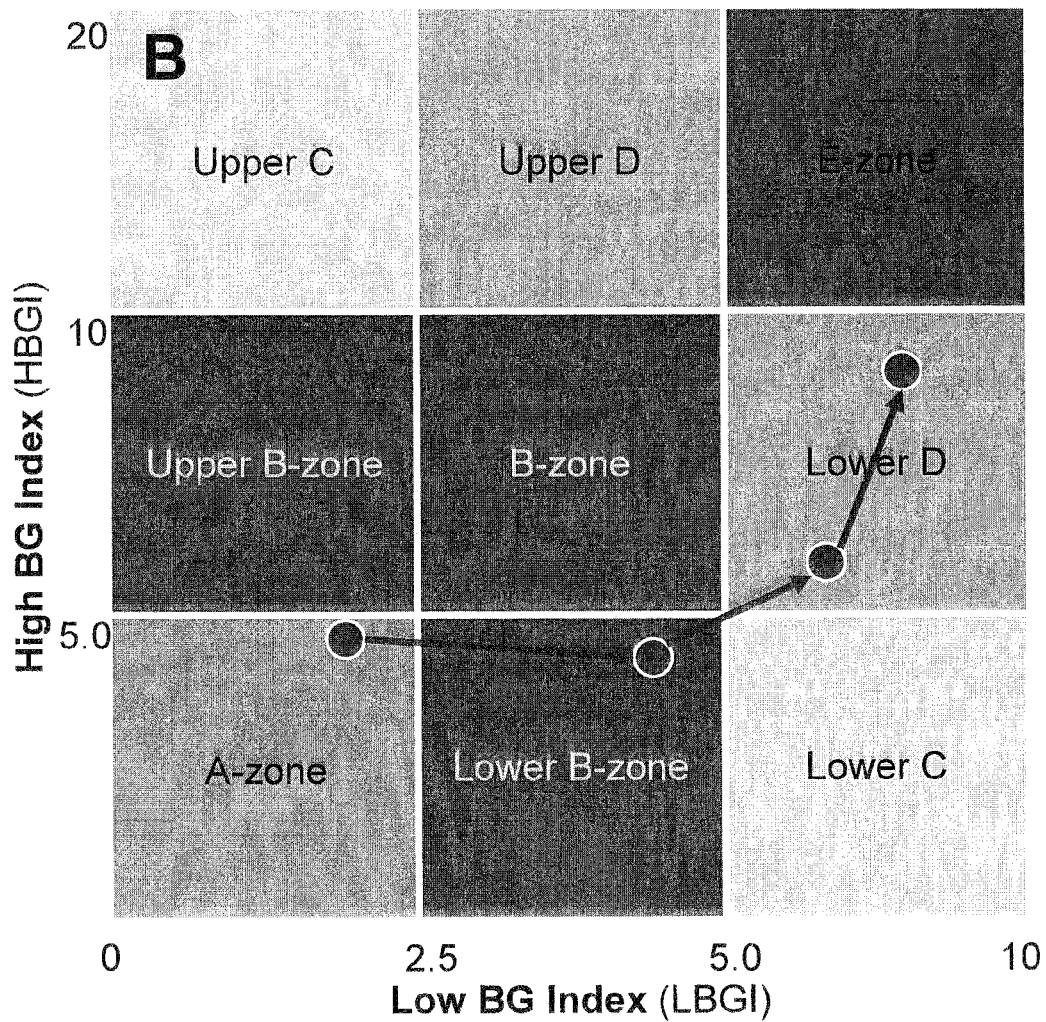

FIG. 15 illustrates an application of the Risk VGA to tracking the risk fluctuation of a particular person over 4 months of SMBG observation. Each data point represents one month of SMBG data. FIG. 15(A) presents a trajectory that indicates a gradual improvement of glucose variability and the associated risks for hypo- and hyperglycemia. FIG. 15(B) presents the opposite trend—presents a trajectory that indicates a gradual deterioration of glucose variability and the associated risks for hypo- and hyperglycemia.

Continuous Glucose Monitoring

An aspect of various embodiments of the present method, system, or computer program product provides, but not limited thereto, a means for analyzing CGM data.

This disclosure discusses, among other things, the mathematical properties of CGM data and the statistical tools and related methods available to analyze both its accuracy and its clinical interpretation.

It shall be noted that the basic unit for most analyses is the glucose trace of an individual, i.e., a time-stamped series of CGM or blood glucose data recorded for each person. Summary characteristics and group-level analyses are derived after the individual traces are processed to produce meaningful individual markers of average glycemia and glucose variation. The analytical methodology is driven by the understanding that BG fluctuations are a continuous process in time, BG(t). Each point of this process is characterized by its value (BG level) and by its rate/direction of BG change. CGM presents the process BG(t) as a discrete time series $\{BG(t_n), n=1, 2, \ldots\}$ that approximates BG(t) in steps determined by the resolution of the particular device (e.g., a reading every 5 min).

Statistical Tools for Interpreting CGM Data: The principal statistical metrics and graphs used to interpret CGM data are described in detail in Clarke & Kovatchev [42]. Here we provide only a brief account of these metrics and graphs in order to distinguish the subject of embodiments of this invention from existing techniques.

Average Glycemia and Deviations from Target

Numerical Measures: The computation of mean glucose value's from CGM data and/or BG data points is straightforward and is suggested as a descriptor of overall glycemic control. Computing of pre- and post-meal averages and their difference can serve as an indication of the overall effectiveness of pre-meal bolus timing and amount. Similarly, the percentages of time spent within, below, or above preset target limits would serve as indication of the general behavior of CGM fluctuations. The suggested limits are 70 and 180 mg/dl, which create 3 clinically different glycemic regions suggested by the DCCT (3) and commonly accepted bands: hypoglycemia (BG≤70 mg/dl) (37); target range (70 mg/dl<BG≤180 mg/dl) and hyperglycemia (BG>180 mg/dl). Percentage of time within additional ranges can be computed as well to emphasize the frequency of extreme glucose excursions. For example, when it is important to distinguish between postprandial and postabsorptive (fasting) conditions, a fasting target range of 70-140 mg/dl is suggested. Further, % of time <50 mg/dl would quantify the frequency of significant hypoglycemia, whereas % of time >300 mg/dl would quantify the frequency of significant hyperglycemia occurring during a clinical trial. Table 4 includes the numerical measures of average glycemia (Table 4A) and deviations from target (Table 4B). All these measures are computed per CGM trace per person, after which they can be used as a base for further group comparisons and other statistical analyses.

TABLE 4

Numerical Measures of Summarizing CGM Data

A: Average Glycemia and Deviations from Target

| | |
|---|---|
| Mean BG | Computed from CGM or blood glucose data for the entire test |
| Mean pre-meal BG | Mean BG restricted to time window 60-0 minutes pre-meals |
| Mean post-meal BG | Mean BG restricted to time window 60-120 minutes post-meals |

B: Deviations from Target

| | |
|---|---|
| % time spent within target range of 70-180 mg/dl; below 70 and above 180 mg/dl. | For CGM, this generally equals to % readings within each of these ranges. For BG measurements that are not equally spaced in time we suggest calculating the % time within each range via linear interpolation between consecutive glucose readings. |
| % time <= 50 mg/dl | Optional, to emphasize occurrence of extreme hypoglycemia; |
| % time > 300 mg/dl | Optional, to emphasize occurrence of extreme hyperglycemia; |

C: Variability and Risk Assessment

| | |
|---|---|
| Inter-Quartile Range | Measure of variability suitable for non-symmetric distributions; |
| BG Risk Index | = LBGI + HBGI-measure of overall variability and risks of hypo- and hyperglycemia. |
| Low BG Index (LBGI) | Measure of the frequency and extent of low BG readings; |
| High BG Index (HBGI) | Measure of the frequency and extent of high BG readings; |
| SD of BG Rate of Change | A measure of the stability of closed-loop control over time; |

D: Events and Other Clinical Characteristics

Events of low BG < 70 mg/dl (or events of BGs < 50 mg/dl);
Events of high BG > 180 mg/dl (or BGs > 300 mg/dl);

Graphs: While plotting the CGM trace observed during the experiment would represent the general pattern of a person's BG fluctuation, additional graphs are suggested to emphasize details of such a pattern corresponding to the numerical measures of the previous section Table 5(A) includes a summary of the suggested graphs.

TABLE 5

Graphs Visualizing CGM Data

A: Average Glycemia and Deviations from Target

| | |
|---|---|
| Glucose trace | Traditional plot of frequently sample glucose data; |
| Aggregated glucose trace | Corresponds to time spent below/within/above a preset target range. Visualizes the crossing of glycemic thresholds; |

B: Variability and Risk Assessment

| | |
|---|---|
| Risk trace | Corresponds to LBGI, HBGI, and BGRI. Designed to equalize the size of glucose deviations towards hypo- and hyperglycemia, emphasize large glucose excursions, and suppress fluctuation within target range, thereby highlighting essential variance; |
| Histogram of BG Rate of Change | Represents the spread and range of glucose transitions. Related to system stability. Corresponds to SD of BG Rate of Change; |
| Poincaré plot | The spread of the data indicates system (patient) stability-more widespread data points are associated with unstable diabetes and rapid glucose fluctuations. |

C: Event-Based Clinical Characteristics

| | |
|---|---|
| Control Variability Grid Analysis | Represents the effectiveness of glycemic control at a group level. Corresponds to event-based characteristics. |

Variability and Risk Assessment

Numerical Measures of Glucose Variability: Computing standard deviation (SD) as a measure of glucose variability of CGM data is not recommended when analyzing BG data because the BG measurement scale is highly asymmetric, the hypoglycemic range is numerically narrower than the hyperglycemic range, and the distribution of the glucose values of an individual is typically quite skewed (18). Therefore SD would be predominantly influenced by hyperglycemic excursions and would not be sensitive to hypoglycemia. It is also possible for confidence intervals based on SD to assume unrealistic negative values. Thus, standard measures such as the interquartile range (IQR) would be more suitable for non-symmetric distributions.

Numerical Measures of Risk: In order to capture both glucose variability and its associated risks for hypo- and hyperglycemia, we have suggested variability and risk measures, as well as risk plots that are based on a symmetrization of the BG measurement scale [18].

We have proposed to compute the LBGI and the HBGI, which in essence split the overall glucose variation into two independent sections related to excursions into hypo- and hyperglycemia, and at the same time equalize the amplitude of these excursions with respect to the risk they carry. For example, in a BG transition from 180 to 250 mg/dl would appear three-fold larger than a transition from 70 to 50 mg/dl, whereas if converted into risk, these fluctuations would appear equal. Using the LBGI, HBGI, and their sum BGRI complements the use of thresholds described above by adding information about the extent of BG fluctuations. Numerical Measures of Patient BG Stability: Analysis of BC rate of change (measured in mg/dl/min) has been suggested as a way to evaluate the dynamics of BG fluctuations on the time scale of minutes. In mathematical terms, this is an evaluation of the "local" properties of the system as opposed to "global" properties discussed above. Table 4C summarizes the suggested measures of glucose variability, system stability, and associated risks.

Graphs:

Table 5B includes a summary of the graphs used to assess the variability and risk of CGM glucose traces. Detailed description is presented in reference [42].

Events and Other Clinical Characteristics

Metrics: CGM data can be used to register the occurrence and the timing of clinically significant events, such as hypoglycemic episodes and events of postprandial hyperglycemia. While there is ongoing discussion whether two consecutive low BG events that are close in time (e.g. 30 min apart) should be considered a single or two separate events, it is suggested that counts of events per day are reported. However, visual inspection of the glucose trace should be employed to see whether discrete events of BG below or above certain threshold can be combined into single event of hypo- or hyperglycemia (see Table 4D).

To visualize the overall glycemic control, in particular glucose extremes, for a group of patients we have introduced the Control Variability Grid Analysis [43], which is built on a min/max plot of CGM values [40] (See Table 5C). [35]

The adoption of these analytical methods would be facilitated if COM manufacturers implement the numerical and graphical displays presented here in their CGM data retrieval software. Accordingly, such displays shall provide valuable information to physician and patients in a condensed easy to interpret format—information that otherwise may remain lost in the complexity of the CGM data stream.

Figure 11:
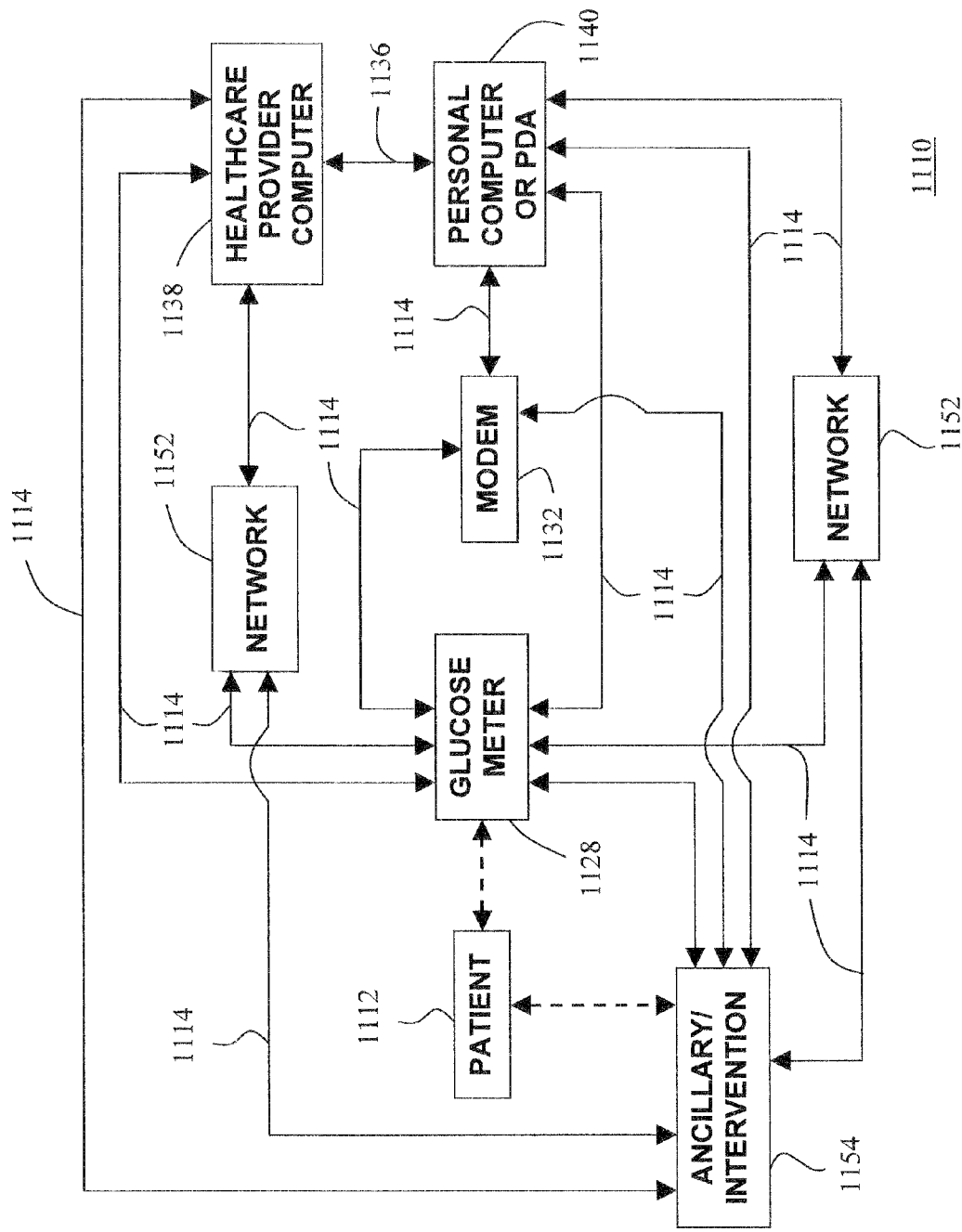
FIG. 11: provides a schematic block diagram of an aspect of an embodiment of the present invention relating processors, communications links, and systems.
Figure 12:
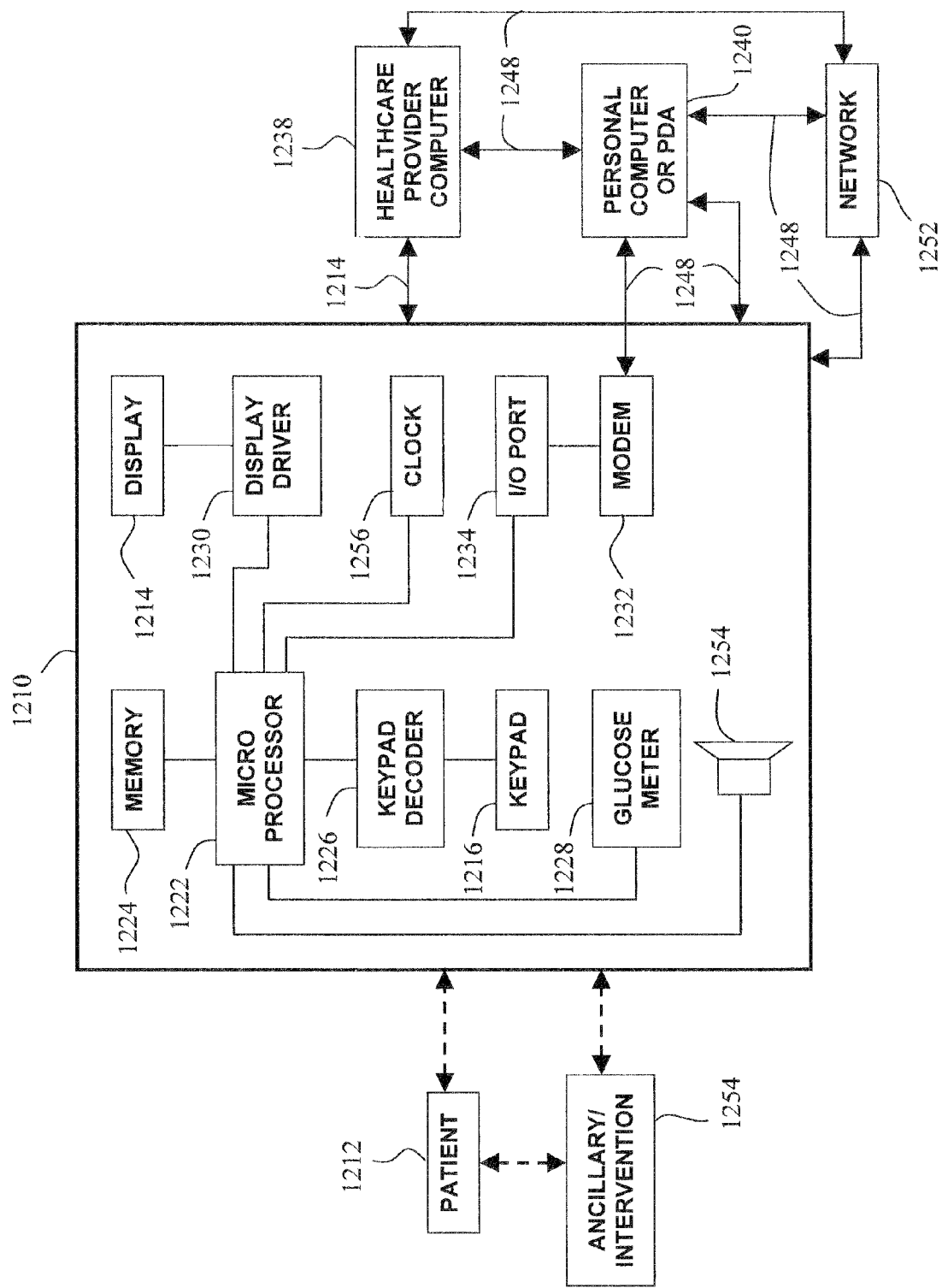
FIG. 12: Provides a schematic block diagram of an aspect of an embodiment of the present invention relating processors, communications links, and systems, for example.
Figure 13:
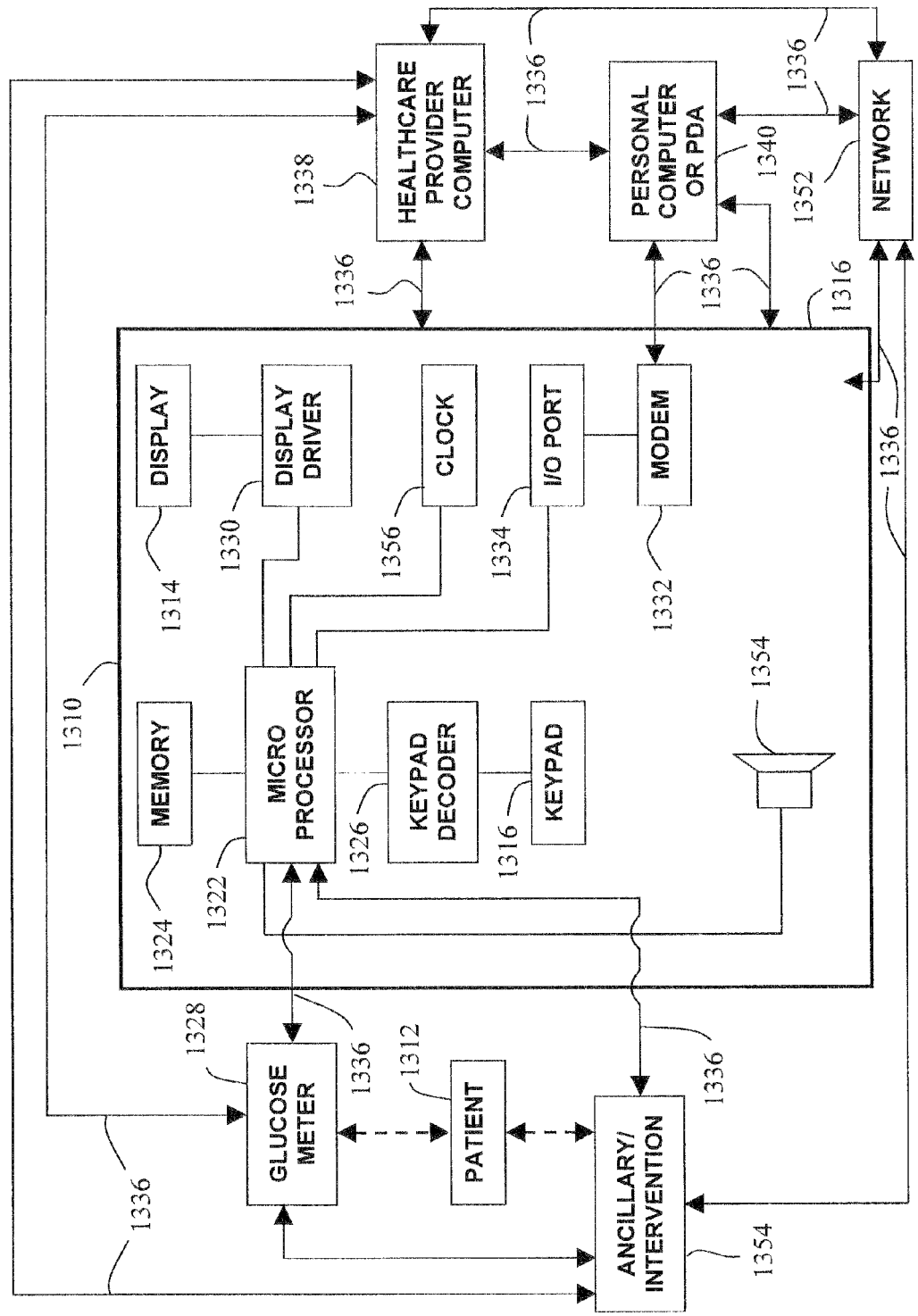
FIG. 13: Provides a schematic block diagram of an aspect of an embodiment of the present invention relating processors, communications links, and systems, for example.

FIGS. 11-13 show block diagrammatic representations of aspects of exemplary embodiments of the present invention. Referring to FIG. 11, there is shown a block diagrammatic representation of the system 1110 essentially comprises the glucose meter 1128 used by a patient 1112 for recording, inter alia, insulin dosage readings and measured blood glucose ("BG") levels. Data obtained by the glucose meter 1128 is preferably transferred through appropriate communication links 1114 or data modem 1132 to a processor, processing station or chip 1140, such as a personal computer, PDA, or cellular telephone, or via appropriate Internet portal. For instance data stored may be stored within the glucose meter 1128 and may be directly downloaded into the personal computer or processor 1140 through an appropriate interface cable and then transmitted via the Internet to a processing location. An example is the ONE TOUCH monitoring system or meter by LifeScan, Inc. which is compatible with IN TOUCH software which includes an interface cable to download the data to a personal computer. It should be appreciated that the glucose meter 1128 and any of the computer processing modules or storage modules may be integral within a single housing or provided in separate housings. The communication link 1114 may be hardwired or wireless. Examples of hardwired may include, but not limited thereto, cable, wire, fiber optic, and/or telephone wire. Examples of wireless may include, but not limited thereto, Bluetooth, cellular phone link, RF link, and/or infrared link. The modules and components of FIGS. 11-13 may be transmitted to the appropriate or desired computer networks (1152, 1252, 1352) in various locations and sites. The modules and components of FIG. 11 may be transmitted to the appropriate or desired computer networks 1152 in various locations and sites (local and/or remote) via desired or required communication links 1114. Moreover, an ancillary or intervention device(s) or system(s) 1154 may be in communication with the patient as well as the glucose meter and any of the other modules and components shown in FIG. 11. Examples of ancillary device(s) and system(s) may include, but not necessarily limited thereto, any combination of one or more of the following: insulin pump, artificial pancreas, insulin device, pulse oximetry sensor, blood pressure sensor, ICP sensor, EMG sensor, EKG sensor, ECG sensor, ECC sensor, pace maker, and heart rate sensor, needle, ultrasound device, or subcutaneous device (as well as any other biometric sensor or device). It should be appreciated that the ancillary or intervention device(s) or system(s) 1154 and glucose meter 1128 may be any sort of physiological or biological communication with the patients (i.e., subject). This physiological or biological communication may be direct or indirect. An indirect communication may include, but not limited thereto, a sample of blood or other biological fluids.

The glucose meter is common in the industry and includes essentially any device that can function as a BG acquisition mechanism. The BG meter or acquisition mechanism, device, tool or system includes various conventional methods directed towards drawing a blood sample (e.g. by fingerprick) for each test, and a determination of the glucose level using an instrument that reads glucose concentrations by electromechanical methods. Recently, various methods for determining the concentration of blood analytes without drawing blood have been developed. For example, U.S. Pat. No. 5,267,152 to Yang et al. (hereby incorporated by reference) describes a noninvasive technique of measuring blood glucose concentration using near-IR radiation diffuse-reflection laser spectroscopy. Similar near-IR spectrometric devices are also described in U.S. Pat. No. 5,086,229 to Rosenthal et al. and U.S. Pat. No. 4,975,581 to Robinson et al. (of which are hereby incorporated by reference).

U.S. Pat. No. 5,139,023 to Stanley (hereby incorporated by reference) describes a transdermal blood glucose monitoring apparatus that relies on a permeability enhancer (e.g., a bile salt) to facilitate transdermal movement of glucose along a concentration gradient established between interstitial fluid and a receiving medium. U.S. Pat. No. 5,036,861 to Sembrowich (hereby incorporated by reference) describes a passive glucose monitor that collects perspiration through a skin patch, where a cholinergic agent is used to stimulate perspiration secretion from the eccrine sweat gland. Similar perspiration collection devices are described in U.S. Pat. No. 5,076,273 to Schoendorfer and U.S. Pat. No. 5,140,985 to Schroeder (of which are hereby incorporated by reference).

In addition, U.S. Pat. No. 5,279,543 to Glikfeld (hereby incorporated by reference) describes the use of iontophoresis to noninvasively sample a substance through skin into a receptacle on the skin surface. Glikfeld teaches that this sampling procedure can be coupled with a glucose-specific biosensor or glucose-specific electrodes in order to monitor blood glucose. Moreover, International Publication No. WO 96/00110 to Tamada (hereby incorporated by reference) describes an iotophoretic apparatus for transdermal monitoring of a target substance, wherein an iotophoretic electrode is used to move an analyte into a collection reservoir and a biosensor is used to detect the target analyte present in the reservoir. Finally, U.S. Pat. No. 6,144,869 to Berner (hereby incorporated by reference) describes a sampling system for measuring the concentration of an analyte present.

Further yet, the BG meter or acquisition mechanism may include indwelling catheters and subcutaneous tissue fluid sampling.

The computer, processor or PDA 1140 may include the software and hardware necessary to process, analyze and interpret the self-recorded or automatically recorded by a clinical assistant device diabetes patient data in accordance with predefined flow sequences and generate an appropriate data interpretation output. The results of the data analysis and interpretation performed upon the stored patient data by the computer or processor 1140 may be displayed in the form of a paper report generated through a printer associated with the personal computer or processor 1140. Alternatively, the results of the data interpretation procedure may be directly displayed on a video display unit associated with the computer or processor 1140. The results additionally may be displayed on a digital or analog display device. The personal computer or processor 1140 may transfer data to a healthcare provider computer 1138 through a communication network 1136. The data transferred through communications network 1136 may include the self-recorded or automated clinical assistant device diabetes patient data or the results of the data interpretation procedure.

FIG. 12 shows a block diagrammatic representation of an alternative embodiment having a diabetes management system that is a patient-operated apparatus or clinical-operated apparatus 1210 having a housing preferably sufficiently compact to enable apparatus 1210 to be hand-held and carried by a patient. A strip guide for receiving a blood glucose test strip (not shown) is located on a surface of housing 1216. Test strip receives a blood sample from the patient 1212. The apparatus may include a microprocessor 1222 and a memory 1224 connected to microprocessor 1222. Microprocessor 1222 is designed to execute a computer program stored in memory 1224 to perform the various calculations and control functions as discussed in greater detail above. A keypad 1216 may be connected to microprocessor 1222 through a standard keypad decoder 1226. Display 1214 may be connected to microprocessor 1222 through a display driver 1230. Display 1214 may be digital and/or analog. Speaker 1254 and a clock 1256 also may be connected to microprocessor 1222. Speaker 1254 operates under the control of microprocessor 1222 to emit audible tones alerting the patient to possible future hypoglycemic or hyperglycemic risks. Clock 1256 supplies the current date and time to microprocessor 1222. Any displays may be visual as well as adapted to be audible.

Memory 1224 also stores blood glucose values of the patient 1212, the insulin dose values, the insulin types, and the parameters used by the microprocessor 1222 to calculate future blood glucose values, supplemental insulin doses, and carbohydrate supplements. Each blood glucose value and insulin dose value may be stored in memory 1224 with a corresponding date and time. Memory 1224 is may be a non-volatile memory, such as an electrically erasable read only memory (EEPROM).

Apparatus 1210 may also include a blood glucose meter 1228 connected to microprocessor 1222. Glucose meter 1228 may be designed to measure blood samples received on blood glucose test strips and to produce blood glucose values from measurements of the blood samples. As mentioned previously, such glucose meters are well known in the art. Glucose meter 1228 is preferably of the type which produces digital values which are output directly to microprocessor 1222. Alternatively, blood glucose meter 1228 may be of the type which produces analog values. In this alternative embodiment, blood glucose meter 1228 is connected to microprocessor 1222 through an analog to digital converter (not shown).

Apparatus 1210 may further include an input/output port 1234, such as a serial port, which is connected to microprocessor 1222. Port 1234 may be connected to a modem 1232 by an interface, such as a standard RS232 interface. Modem 1232 is for establishing a communication link 1248 between apparatus 1210 and a personal computer 1240 or a healthcare provider computer 1238 through a communication link 1248. The modules and components of FIG. 12 may be transmitted to the appropriate or desired computer networks 1252 in various locations and sites (local and/or remote) via desired or required communication links 1248. Moreover, an ancillary or intervention device(s) or system(s) 1254 may be in communication with the patient as well as the glucose meter and any of the other modules and components shown in FIG. 12. Examples of ancillary device(s) and system(s) may include, but not necessarily limited thereto any combination of one or more of the following: insulin pump, artificial pancreas, insulin device, pulse oximetry sensor, blood pressure sensor, ICP sensor, EMG sensor, EKG sensor, ECG sensor, ECC sensor, pace maker, heart rate sensor, needle, ultrasound device, or subcutaneous device (as well as any other biometric sensor or device). It should be appreciated that the ancillary or intervention device(s) or system(s) 1254 and glucose meter 1228 may be any sort of physiological or biological communication with the patients (i.e., subject). This physiological or biological communication may be direct or indirect. An indirect communication may include, but not limited thereto, a sample of blood or other biological fluids. Specific techniques for connecting electronic devices, systems and software through connections, hardwired or wireless, are well known in the art. Another alternative example is "Bluetooth" technology communication.

Alternatively, FIG. 13 shows a block diagrammatic representation of an alternative embodiment having a diabetes management system that is a patient-operated apparatus 1310, similar to the apparatus as shown in FIG. 12, having a housing preferably sufficiently compact to enable the apparatus 1310 to be hand-held and carried by a patient. For example, a separate or detachable glucose meter or BG acquisition mechanism/module 1328. The modules and components of FIG. 13 may be transmitted to the appropriate or desired computer networks 1352 in various locations and sites (local and/or remote) via desired or required communication links 1336. Moreover, an ancillary or intervention device(s) or system(s) 1354 may be in communication with the patient as well as the glucose meter and any of the other modules and components shown in FIG. 13. Examples of ancillary device(s) and system(s) may include, but not necessarily limited thereto any combination of one or more of the following: insulin pump, artificial pancreas, insulin device, pulse oximetry sensor, blood pressure sensor, ICP sensor, EMG sensor, EKG sensor, ECG sensor, ECC sensor, pace maker, heart rate sensor needle, ultrasound device, or subcutaneous device (as well as any other biometric sensor or device). It should be appreciated that the ancillary or intervention device(s) or system(s) 1354 and glucose meter 1328 may be any sort of physiological or biological communication with the patients (i.e., subject). This physiological or biological communication may be direct or indirect. An indirect communication may include, but not limited thereto, a sample of blood or other biological fluids. There are already self-monitoring devices that are capable of directly computing the algorithms disclosed in this application and displaying the results to the patient without transmitting the data to anything else. Examples of such devices are ULTRA SMART by LifeScan, Inc., Milpitas, Calif. and FREESTYLE TRACKER by Therasense, Alameda, Calif.

It should be appreciated that the various blood glucose meters, systems, method and computer program products discussed herein are applicable for SMBG and CGM.

Accordingly, various blood glucose meters, systems, and methods may be utilized with the various embodiments of the present invention. For example, SMBG devices may include: OneTouch (several different meters) from LifeScan, Inc; Freestyle (several meters) from Abbott Diabetes care; Contour from Bayer, and Accu-chek (several meters) from Roche Diagnostics, or other available SMBG devices. For example, CGM devices may include: Guardian and Paradigm from Medtronic; Freestyle navigator (Abbott Diabetes Care); and Dexcom Seven from Dexcom, Inc., or other available CGM devices.

Accordingly, the embodiments described herein are capable of being implemented over data communication networks such as the internet, making evaluations, estimates, and information accessible to any processor or computer at any remote location, as depicted in FIGS. 11-13 and/or U.S. Pat. No. 5,851,186 to Wood, of which is hereby incorporated by reference herein. Alternatively, patients located at remote locations may have the BG data transmitted to a central healthcare provider or residence, or a different remote location.

It should be appreciated that any of the components/modules discussed in FIGS. 11-13 may be integrally contained within one or more housings or separated and/or duplicated in different housings. Similarly, any of the components discussed in FIGS. 11-13 may be duplicated more than once. Moreover, various components and modules may be adapted to replace another component or module to perform the intended function.

It should also be appreciated that any of the components/modules present in FIGS. 11-13 may be in direct or indirect communication with any of the other components/modules.

It should be appreciated that the healthcare provide computer module as depicted in FIGS. 11-13 may be any location, person, staff, physician, caregiver, system, device or equipment at any healthcare provider, hospital, clinic, university, vehicle, trailer, or home, as well as any other location, premises, or organization as desired or required.

It should be appreciated that as discussed herein, a patient or subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example. The patient or subject may be applicable for, but not limited thereto, any desired or required treatment, study, diagnosis, monitoring, tracking, therapy or care.

Figure 14:
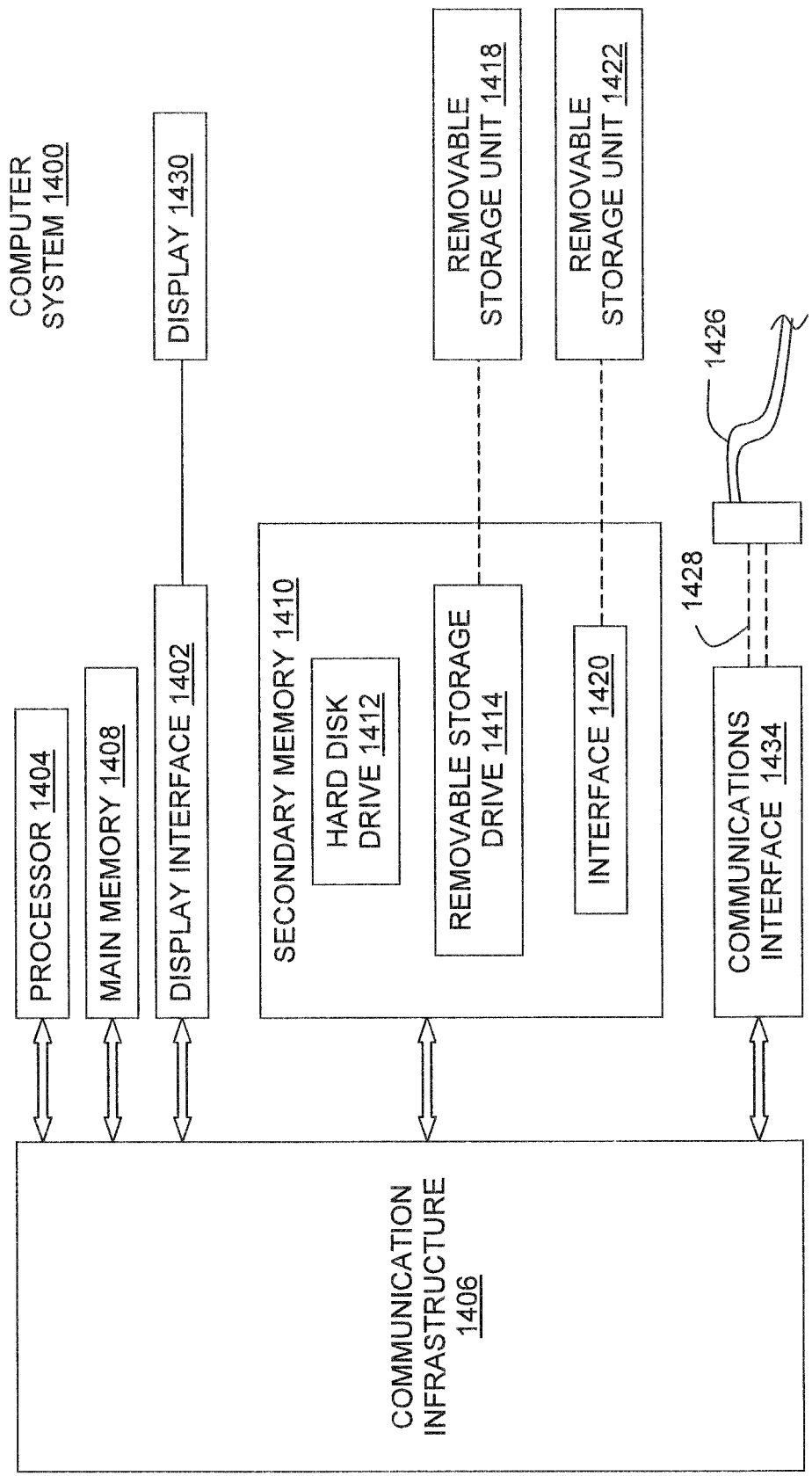
FIG. 14: Provides a schematic block diagram for an aspect of a system or related method of an aspect of an embodiment of the present invention.

FIG. 14 is a functional block diagram for a computer system 1400 for implementation of an exemplary embodiment or portion of an embodiment of present invention. For example, a method or system of an embodiment of the present invention may be implemented using hardware, software or a combination thereof and may be implemented in one or more computer systems or other processing systems, such as personal digit assistants (PDAs) equipped with adequate memory and processing capabilities. In an example embodiment, the invention was implemented in software running on a general purpose computer as illustrated in FIG. 14. The computer system 1400 may includes one or more processors, such as processor 1404. The Processor 1404 is connected to a communication infrastructure 1406 (e.g., a communications bus, cross-over bar, or network). The computer system 1400 may include a display interface 1402 that forwards graphics, text, and/or other data from the communication infrastructure 1406 (or from a frame buffer not shown) for display on the display unit 1430. Display unit 1430 may be digital and/or analog.

The computer system 1400 may also include a main memory 1408, preferably random access memory (RAM), and may also include a secondary memory 1410. The secondary memory 1410 may include, for example, a hard disk drive 1412 and/or a removable storage drive 1414, representing a floppy disk drive, a magnetic tape drive, an optical disk drive, a flash memory, etc. The removable storage drive 1414 reads from and/or writes to a removable storage unit 1418 in a well known manner. Removable storage unit 1418, represents a floppy disk, magnetic tape, optical disk, etc. which is read by and written to by removable storage drive 1414. As will be appreciated, the removable storage unit 1418 includes a computer usable storage medium having stored therein computer software and/or data.

In alternative embodiments, secondary memory 1410 may include other means for allowing computer programs or other instructions to be loaded into computer system 1400. Such means may include, for example, a removable storage unit 1422 and an interface 1420. Examples of such removable storage units/interfaces include a program cartridge and cartridge interface (such as that found in video game devices), a removable memory chip (such as a ROM, PROM, EPROM or EEPROM) and associated socket, and other removable storage units 1422 and interfaces 1420 which allow software and data to be transferred from the removable storage unit 1422 to computer system 1400.

The computer system 1400 may also include a communications interface 1424. Communications interface 1424 allows software and data to be transferred between computer system 1400 and external devices. Examples of communications interface 1424 may include a modem, a network interface (such as an Ethernet card), a communications port (e.g., serial or parallel, etc.), a PCMCIA slot and card, a modem, etc. Software and data transferred via communications interface 1424 are in the form of signals 1428 which may be electronic, electromagnetic, optical or other signals capable of being received by communications interface 1424. Signals 1428 are provided to communications interface 1424 via a communications path (i.e., channel) 1426. Channel 1426 (or any other communication means or channel disclosed herein) carries signals 1428 and may be implemented using wire or cable, fiber optics, blue tooth, a phone line, a cellular phone link, an RF link, an infrared link, wireless link or connection and other communications channels.

In this document, the terms "computer program medium" and "computer usable medium" are used to generally refer to media or medium such as various software, firmware, disks, drives, removable storage drive 1414, a hard disk installed in hard disk drive 1412, and signals 1428. These computer program products ("computer program medium" and "computer usable medium") are means for providing software to computer system 1400. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 1408 and/or secondary memory 1410. Computer programs may also be received via communications interface 1424. Such computer programs, when executed, enable computer system 1400 to perform the features of the present invention as discussed herein. In particular, the computer programs, when executed, enable processor 1404 to perform the functions of the present invention. Accordingly, such computer programs represent controllers of computer system 1400.

In an embodiment where the invention is implemented using software, the software may be stored in a computer program product and loaded into computer system 1400 using removable storage drive 1414, hard drive 1412 or communications interface 1424. The control logic (software or computer program logic), when executed by the processor 1404, causes the processor 1404 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

Experimental Software Implementing the Min/Max VGA

Figure 16:
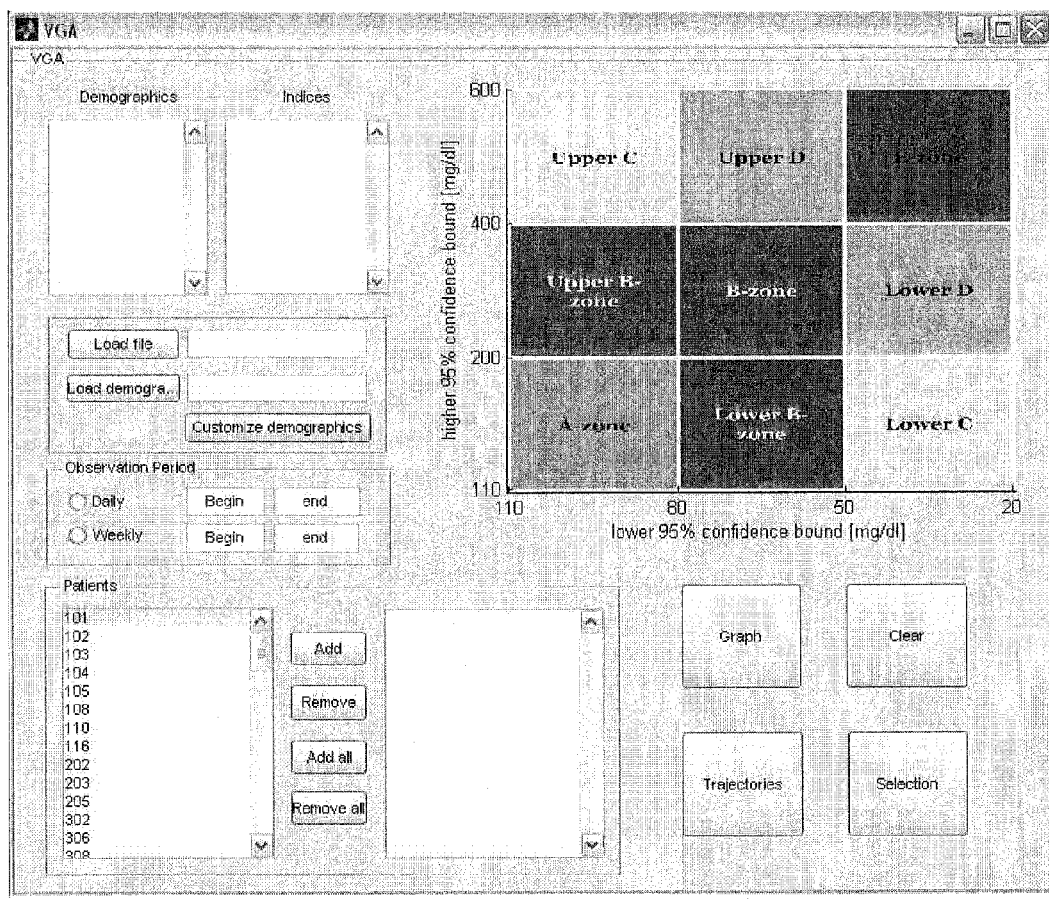
FIG. 16: Provides a screenshot of an example of an embodiment of the variability tracking software.
Figure 17A:
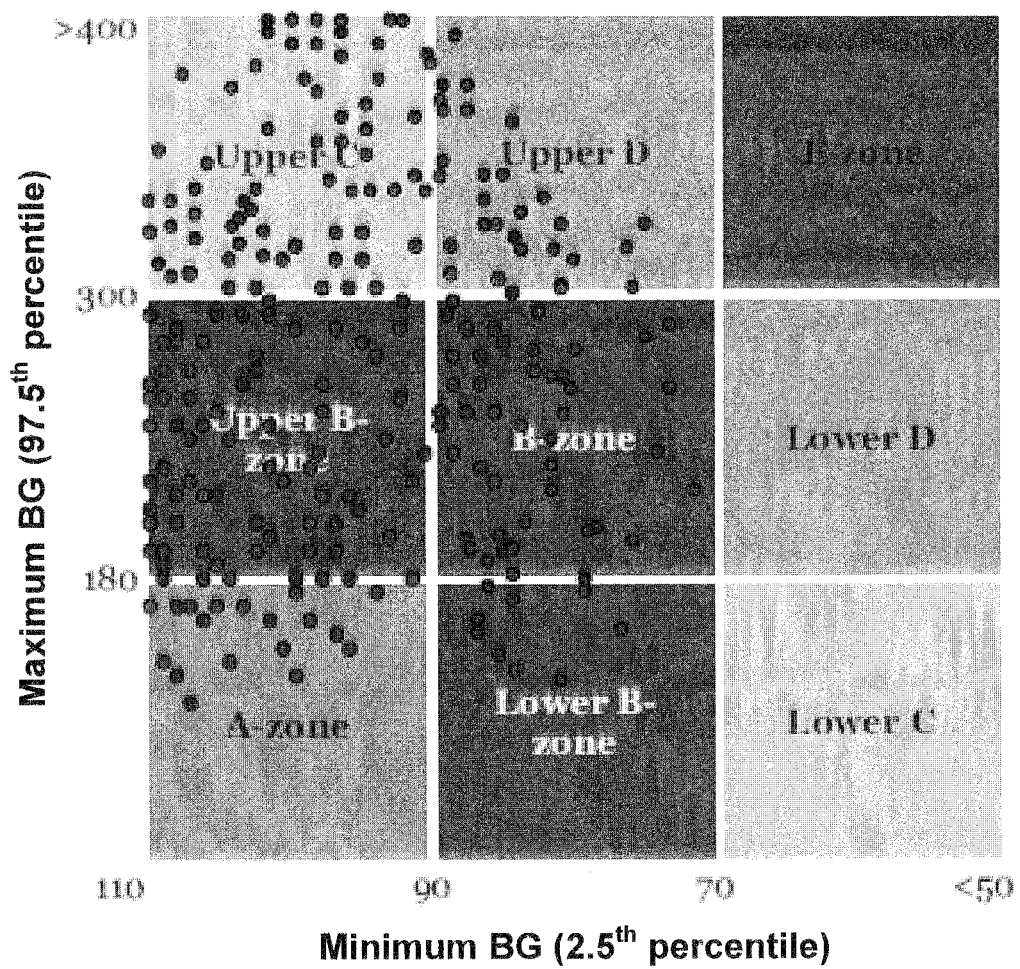
FIG. 17: Provides an embodiment of the Control Variability Grid Analysis for Patients Prone to Overcorrecting Hypoglycemia and Patients Prone to Overcorrecting Hyperglycemia for FIGS. 17(A) and 17(B), respectfully.
Figure 17B:
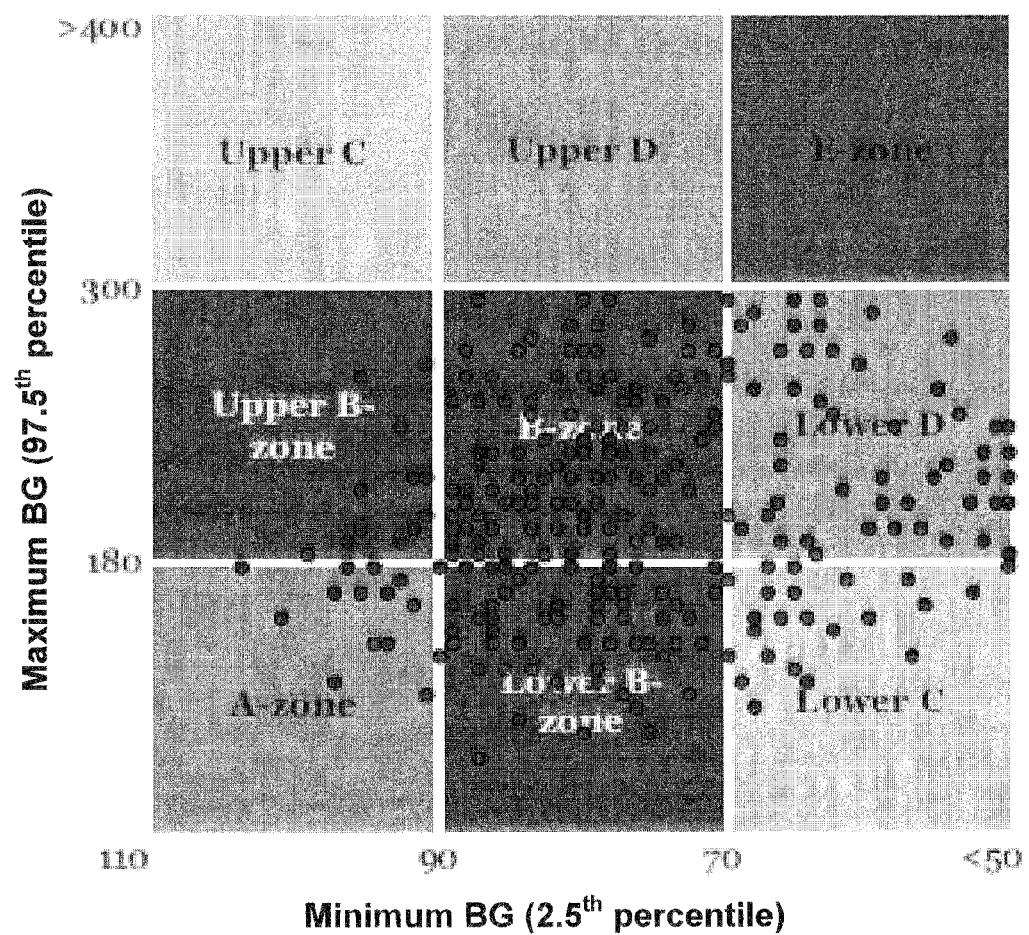

Experimental software has been developed (using MATLAB®) to illustrate one variant of the VGA method—the Min/Max VGA. The software allows for displaying individual trajectories and populations to illustrate the concept of glucose variability tracking, and includes extraction and tracking over time at an individual level of relevant characteristics of glucose variability and associated hypo- and hyperglycemic extremes. FIG. 16 shows a screenshot of an example of variability tracking software according to one embodiment of the present invention.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

REFERENCES CITED

The following patents, applications and publications as listed below and throughout this document are hereby incorporated by reference in their entirety herein.

The devices, systems, compositions and methods of various embodiments of the invention disclosed herein may utilize aspects disclosed in the following references, applications, publications and patents and which are hereby incorporated by reference herein in their entirety:

1. Aaby Svendsen P, Lauritzen. T, Soegard U, Nerup J. Glycosylated Haemoglobin and Steady-State Mean Blood Glucose Concentration in Type 1 (Insulin-Dependent) Diabetes. *Diabetologia,* 23: 403-405, 1982.
2. Santiago J V. Lessons from the Diabetes Control and Complications Trial, *Diabetes,* 42:1549-1554, 1993
3. The Diabetes Control and Complications Trial Research Group. The effect of intensive treatment of diabetes on the development and progression of long-term complications of insulin-dependent diabetes mellitus. *N Engl J Med* 329: 978-986, 1993
4. UK Prospective Diabetes Study Group (UKPDS). Intensive blood-glucose control with sulphonylureas or insulin compared with conventional treatment and risk of complications in patients with type 2 diabetes. *Lancet* 352: 837-853, 1998
5. The Diabetes Control and Complications Trial Research Group: The relationship of glycemic exposure (HbA1c) to the risk of development and progression of retinopathy in the Diabetes Control and Complications Trial. *Diabetes* 44:968-983, 1995

6. Brownlee M, Hirsh I B. Glycemic Variability: A hemoglobin A1c—Independent Risk Factor for Diabetic Complication? *JAMA* 2006 295: 1707-1708.

7. The Diabetes Control and Complications Trial Research Group. Hypoglycemia in the Diabetes Control and Complications Trial. *Diabetes* 46: 271-286, 1997

8. Henderson J N, Allen K V, Deary I J, Frier B M. Hypoglycemia in insulin-treated Type 2 diabetes: frequency, symptoms and impaired awareness. *Diabet Med* 20: 1016-1021, 2003

9. Cryer P E. Iatrogenic hypoglycemia as a cause of hypoglycemia-associated autonomic failure in IDDM: A vicious cycle. *Diabetes* 41:255-260, 1992

10. Segel S A, Paramore D S, Cryer P E. Hypoglycemia-associated autonomic failure in advanced type 2 diabetes. *Diabetes* 51: 724-733, 2002

11. Gold A E, Deary I J, Frier B M. Recurrent severe hypoglycemia and cognitive function in type I diabetes. *Diabet Med* 10:503-508, 1993

12. Cryer P E. Hypoglycemia: The limiting factor in the glycemic management of type I and type II diabetes. *Diabetologia* 45: 937-948, 2002

13. American. Diabetes Association. Postprandial Blood Glucose: Consensus Statement. *Diabetes Care* 24: 775-778, 2001.

14. Basu A., Alzaid A., Dinneen S., Caumo A., Cobelli C., Rizza R.: Effects of a change in the pattern of insulin delivery on carbohydrate tolerance in diabetic and nondiabetic humans in the presence of differing degrees of insulin resistance. *J Clin Invest* 97:2351-2361, 1996

15. Schlichtkrull J, Munck O, Jersild M. The M-value, an index of blood glucose control in diabetics. *Acta Med Scand* 177: 95-102, 1965

16. Service F J, Molner G D, Rosevear J W, Ackerman E, Gatewood L C, Taylor W F. Mean amplitude of glycemic excursions, a measure of diabetic instability *Diabetes* 19: 644-655, 1970

17. Ryan E A, Shandro T, Green K, Paty B W, Senior P A, Bigam D, Shapiro A M J, Vantyghem M C. Assessment of the Severity of Hypoglycemia and Glycemic Lability in Type 1 Diabetic Subjects Undergoing Islet Transplantation *Diabetes* 53: 955-962, 2004

18. Kovatchev B P, Cox D J, Gonder-Frederick L A and W L Clarke. Symmetrization of the blood glucose measurement scale and its applications. *Diabetes Care* 20: 1655-1658, 1997.

19. Saudek. C D, Derr R L, Kalyani R R. Assessing Glycemia in Diabetes Using Self-monitoring Blood Glucose and Hemoglobin A1e. *JAMA* 2006 295: 1688-1697.

20. Klonoff D C: Continuous glucose monitoring: roadmap for $21_{st}$ century diabetes therapy. Diabetes Care 2005; 28:1231-1239.

21. Kovatchev B P, Straume M, Cox D J, Farhy L S. Risk analysis of blood glucose data: A quantitative approach to optimizing the control of insulin dependent diabetes. *J of Theoretical Medicine,* 3:1-10, 2001.

22. Kovatchev B P, Cox D J, Straume M, Farhy L S. Association of Self-monitoring Blood Glucose Profiles with Glycosylated Hemoglobin (2000). In: Methods in Enzymology, vol. 321: Numerical Computer Methods, Part C: 410-417 M. Johnson & L. Brand, Eds., Academic Press, NY.

23. Kovatchev B P, Clarke W L, Breton M, Brayman K, McCall A. Quantifying Temporal Glucose Variability in Diabetes via Continuous Glucose Monitoring: Mathematical Methods and Clinical Application. *Diabetes Technology and Therapeutics,* 7: 849-862, 2005.

24. McCali A L, Kovatchev B P, Cox D J, Crean J, Maggs D, Gloster M. Assessing glucose variability using CGMS in pramlintide- and placebo-treated subjects with Type 1 diabetes mellitus. *Diabetologia,* 47, Supplement 1: A283, 2004

25. Kovatchev B P, Otto E, Cox D J, Gonder-Frederick L A, Clarke W L. Evaluation of a New Measure of Blood Glucose Variability in Diabetes. Diabetes Care, 29: 2433-2438, 2006.

26. Kovatchev B P, Cox D J, Gonder-Frederick L A and W L Clarke (2002). Methods for quantifying self-monitoring blood glucose profiles exemplified by an examination of blood glucose patterns in patients with Type 1 and Type 2 Diabetes. Diabetes Technology and Therapeutics, 4 (3): 295-303.

27. Kovatchev B P, Cox D J, Kumar A, Gonder-Frederick L A, Clarke W L (2003). Algorithmic Evaluation of Metabolic Control and Risk of Severe Hypoglycemia in Type 1 and Type 2 Diabetes Using Self-Monitoring Blood Glucose (SMBG) Data. Diabetes Technology and Therapeutics, 5 (5): 817-828.

28. Kovatchev B P, Cox D J, Gonder-Frederick L A Young-Hyman D, Schlundt D and W L Clarke (1998). Assessment of Risk for Severe Hypoglycemia Among Adults with IDDM: Validation of the Low Blood Glucose Index, Diabetes Care, 21: 1870-1875. 29. S. P. Meyn and R. L. Tweedie. *Markov Chains and Stochastic Stability.* London: Springer-Verlag, 1993.

29. Food and Drug Administration. Summary of Safety and Effectiveness Data—Medtronic Guardian RT. www.fda.gov/cdrh/PDF/p980022s01.pdf; 2006.

30. Food and Drug Administration. Summary of Safety and Effectiveness Data—STS-7 Continuous Glucose Monitoring System www.fda.gov/crdh/pdf5/p050012s001b.pdf 2007

31. Food and Drug Administration. Summary of Safety and Effectiveness Data—FreeStyle Navigator Continuous Glucose Monitoring System. www.fda.gov/crdh/pdf5/p050020b.pdf 2008

32. Kovatchev, B., Gonder-Frederick, L., Cox, D., Clarke, W.: Evaluating the Accuracy of Continuous Glucose Monitoring Sensors. Diabetes Care 27:1922-1928, 2004

33. Cox, D; Herrman, J; Snyder, A; Gonder-Frederick, L; Reschke, J; Clarke, W: Stability of reacted Chemstrip bG. Diabetes Care, 11:288-291, 1988.

34. American Diabetes Association Workgroup on Hypoglycemia: Defining and Reporting Hypoglycemia in Diabetes: A report from the American Diabetes Association Workgroup on Hypoglycemia. *Diabetes Care* 28: 1245-1249, 2005.

35. Kovatchev B P, Straume M, Cox D J, Farhi L S: Risk analysis of blood glucose data: a quantitative approach to optimizing the control of insulin dependent diabetes. J Theor Med, 3:1-10, 2001.

36. Miller M, Strange P: Use of Fourier Models for Analysis and Interpretation of Continuous Glucose Monitoring Glucose Profiles. *J Diabetes Sci Technol,* 1: 630-638, 2007.

37. Shields D, Breton M. Blood vs. Interstitial Glucose Dynamic Fluctuations: The Nyquist Frequency of Continuous Glucose Monitors. Proc. $7^{th}$ Diabetes Technol Mtg, 2007.

38. McDonnell C M, Donath S M, Vidmar S I, Werther G A, Cameron F J: A Novel Approach to Continuous Glucose Analysis Utilizing Glycemic Variation. *Diabetes Technol Ther,* 7: 253-263, 2005.

39. Brennan M, Palaniswami M, Kamen P: Do existing measures of Poincare plot geometry reflect nonlinear features of heart rate variability? *IEEE Trans Biomed Eng,* 48:1342-1347, 2001.
40. Magni L, Raimondo F, Dalla Man C, Breton M D, Patek S, D e Nicolao G, Cobelli C, and Kovatchev B P (2008). Evaluating the Efficacy of Closed-Loop Glucose Regulation via Control-Variability Grid Analysis. J Diabetes Sci Technol, 2: 630-635.
41. Kovatchev B P, Breton M D, Dalla Man C, Cobelli C (2009). In Silico Preclinical Trials: A Proof of Concept in Closed-Loop Control of Type 1 Diabetes. *J Diabetes Sci Technol* 3: 44-55.
42. Clarke W L & Kovatchev B P (2009). Statistical Tools to Analyze CGM Data. *Diabetes Technology and Therapeutics,* 11: S45-S54.

ADDITIONAL REFERENCES

The following patents, applications and publications as listed below are hereby incorporated by reference in their entirety herein.

The devices, systems, computer program product and methods of various embodiments of the invention disclosed herein may utilize aspects disclosed in the following references, applications, publications and patents and which are hereby incorporated by reference herein in their entirety:

1. PCT/US2008/082063, entitled "Model Predictive Control Based Method for Closed-Loop Control of Insulin Delivery in Diabetes Using Continuous Glucose Sensing", filed Oct. 31, 2008.
2. PCT/US2008/069416, entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008.
3. PCT/US2008/067725, entitled "Method, System and Computer Simulation Environment for Testing of Monitoring and Control Strategies in Diabetes," filed Jun. 20, 2008.
4. PCT/US2008/067723, entitled "LQG Artificial Pancreas Control System and Related Method", filed on Jun. 20, 2008.
5. U.S. Ser. No. 12/516,044, filed May 22, 2009, entitled "Method, System, and Computer Program Product for the Detection of Physical Activity by Changes in Heart Rate, Assessment of Fast Changing Metabolic States, and Applications of Closed and Open Control Loop in Diabetes;"
6. PCT/US2007/085588 not yet published filed Nov. 27, 2007, entitled "Method, System, and Computer Program Product for the Detection of Physical Activity by Changes in Heart Rate, Assessment of Fast Changing Metabolic States, and Applications of Closed and Open Control Loop in Diabetes;"
7. U.S. Ser. No. 11/943,226, filed Nov. 20, 2007, entitled "Systems, Methods and Computer Program Codes for Recognition of Patterns of Hyperglycemia and Hypoglycemia, Increased Glucose Variability, and Ineffective Self-Monitoring in Diabetes;"
8. U.S. patent application Ser. No. 11/578,831, filed Oct. 18, 2006 entitled "Method, System and Computer Program Product for Evaluating the Accuracy of Blood Glucose Monitoring Sensors/Devices".
9. PCT International Application Serial No. PCT/US2005/013792, filed Apr. 21, 2005, entitled "Method, System, and Computer Program Product for Evaluation of the Accuracy of Blood Glucose Monitoring Sensors/Devices;"
10. PCT International Application Serial No. PCT/US01/09884, filed Mar. 29, 2001, entitled "Method, System, and Computer Program Product for Evaluation of Glycemic Control in Diabetes Self-Monitoring Data;"
11. U.S. Pat. No. 7,025,425 B2 issued Apr. 11, 2006, entitled "Method, System, and Computer Program Product for the Evaluation of Glycemic Control in Diabetes from Self-Monitoring Data;"
12. U.S. patent application Ser. No. 11/305,946 filed Dec. 19, 2005 entitled "Method, System, and Computer Program Product for the Evaluation of Glycemic Control in Diabetes from Self-Monitoring Data" (Publication No. 2006/0094947);
13. PCI International. Application Serial No. PCT/US2003/025053, filed Aug. 8, 2003, entitled "Method, System, and Computer Program Product for the Processing of Self-Monitoring Blood Glucose (SMBG) Data to Enhance Diabetic Self-Management;"
14. U.S. patent application Ser. No. 10/524,094 filed Feb. 9, 2005 entitled "Managing and Processing Self-Monitoring Blood Glucose" (Publication No. 2005/214892);
15. U.S. Ser. No. 12/065,257, filed Aug. 29, 2008, entitled "Accuracy of Continuous Glucose Sensors;"
16. PCT International Application Serial No PCT/US2006/033724, filed Aug. 29, 2006, entitled "Method for Improvising Accuracy of Continuous Glucose Sensors and a Continuous Glucose Sensor Using the Same;"
17. U.S. Ser. No. 12/159,891, filed Jul. 2, 2008, entitled "Method, System and Computer Program Product for Evaluation of Blood Glucose Variability in Diabetes from Self-Monitoring Data;"
18. PCT International Application No. PCT/US2007/000370, filed Jan. 5, 2007, entitled "Method, System and Computer Program Product for Evaluation of Blood Glucose Variability in Diabetes from Self-Monitoring Data;"
19. U.S. patent application Ser. No. 11/925,689 and PCT International Patent Application No. PCT/US2007/082744, both filed Oct. 26, 2007, entitled "For Method, System and Computer Program Product for Real-Time Detection of Sensitivity Decline in Analyte Sensors."
20. U.S. Ser. No. 10/069,674, filed Feb. 22, 2002, entitled "Method and Apparatus for Predicting the Risk of Hypoglycemia;"
21. PCT International Application No. PCT/US00/22886, filed Aug. 21, 2000, entitled "Method and Apparatus for Predicting the Risk of Hypoglycemia;" and
22. U.S. Pat. No. 6,923,763 B1, issued Aug. 2, 2005, entitled "Method and Apparatus for Predicting the Risk of Hypoglycemia;"

What is claimed is:
1. A system for visually tracking blood glucose variability in diabetes in a subject, said system comprising:
   an acquisition module acquiring a plurality of blood glucose data of the subject over a predefined period of time;
   a processor programmed to
      compute blood glucose variability of the subject over said predefined period of time using said blood glucose data; and
      plot the computed blood glucose variability on an output display in the form of data points on a graph having a coordinate system representing hypoglycemic risk along one axis of said graph and hyperglycemic risk along another axis of said graph;
   wherein the location of a data point in said coordinate system of said graph represents a variable degree of control of blood glucose levels of said subject; and wherein said tracking provides an area of optimal glucose control in said graph, and provides areas in said graph indicating risk for hyperglycemia and hypoglycemia.

2. The system of claim 1, wherein said graph comprises:
a first axis representing the risk for hypoglycemia; and
a second axis representing the risk for hyperglycemia.

3. The system of claim 1, wherein said graph comprises:
a first axis representing the Low Blood Glucose Index (LBGI); and
a second axis representing the High Blood Glucose Index (HBGI).

4. The system of claim 1, wherein said graph comprises:
a first axis representing the inverse-coded lower percentile; and
a second axis representing the upper percentile.

5. The system claim 1, wherein said graph comprises at least one of:
a first zone representing the optimal control of glucose variability;
a second zone representing moderate deviations into hypoglycemia, but good control of hyperglycemia;
a third zone representing moderate deviations into hyperglycemia, but good control of hypoglycemia;
a fourth zone representing moderate deviations towards both hypoglycemia and hyperglycemia;
a fifth zone representing over-correction of hyperglycemia;
a sixth zone representing over-correction of hypoglycemia;
a seventh zone representing failure to deal with hypoglycemia;
an eighth zone representing failure to deal with hyperglycemia; and
a ninth zone representing an erroneous control.

6. The system of claim 2, wherein said first axis comprises about the inverse-coded 2.5% of a distribution of said blood glucose data and the second axis comprises about the 97.5% of a distribution of said blood glucose data.

7. The system of claim 2, wherein said first axis comprises about the 97.5% of a distribution of said blood glucose data and the second axis comprises about the inverse-coded 2.5% of a distribution of said blood glucose data.

8. The system of claim 5, wherein said graph comprises:
said first zone further comprises said first axis ranging from about 110-80 mg/dl and said second axis ranging from about 110-200 mg/dl;
said second zone further comprises said first axis ranging from about 80-50 mg/dl and said second axis ranging from about 110-200 mg/dl;
said third zone further comprises said first axis ranging from about 110-80 mg/dl and said second axis ranging from about 200-400 mg/dl;
said fourth zone further comprises said first axis ranging from about 80-50 mg/dl and said second axis ranging from about 200-400 mg/dl;
said fifth zone further comprises said first axis ranging from about less than 50 mg/dl and said second axis ranging from about 110-200 mg/dl;
said sixth zone further comprises said first axis ranging from about 110-80 mg/dl and said second axis ranging from about greater than 400 mg/dl;
said seventh zone further comprises said first axis ranging from about less than 50 mg/dl and said second axis ranging from about 200-400 mg/dl;
said eighth zone further comprises said first axis ranging from about 80-50 mg/dl and said second axis ranging from about greater than 400 mg/dl; and
said ninth zone further comprises said first axis ranging from about less than 50 mg/dl and said second axis ranging from about greater than 400 mg/dl.

9. The system of claim 4, wherein said first axis comprises about the inverse-coded 25% and the second axis comprises about the 75% of said blood glucose data.

10. The system of claim 4, wherein said second axis comprises about the inverse-coded 25% and the first axis comprises about the 75% of said blood glucose data.

11. The system of claim 5, wherein:
said first zone further comprises said first axis ranging from about 110-90 mg/dl and said second axis ranging from about 110-180 mg/dl;
said second zone further comprises said first axis ranging from about 90-70 mg/dl and said second axis ranging from about 110-180 mg/dl;
said third zone further comprises said first axis ranging from about 110-90 mg/dl and said second axis ranging from about 180-250 mg/dl;
said fourth zone further comprises said first axis ranging from about 90-70 mg/dl and said second axis ranging from about 180-250 mg/dl;
said fifth zone further comprises said first axis ranging from about less than 70 mg/dl and said second axis ranging from about 110-180 mg/dl;
said sixth zone further comprises said first axis ranging from about 110-90 mg/dl and said second axis ranging from about greater than 250 mg/dl;
said seventh zone further comprises said first axis ranging from about less than 70 mg/dl and said second axis ranging from about 180-250 mg/dl;
said eighth zone further comprises said first axis ranging from about 90-70 mg/dl and said second axis ranging from about greater than 250 mg/dl; and
said ninth zone further comprises said first axis ranging from about less than 70 mg/dl and said second axis ranging from about greater than 250 mg/dl.

12. The system of claim 3, wherein said first axis comprises a Low Blood Glucose Index (LBGI) of said blood glucose data.

13. The system of claim 12, wherein said Low Blood Glucose Index (LBGI) is provided by:

$$LBGI_k^t = \frac{1}{n_k^t}\sum_{s=1}^{n_k^t} rl(x_{ks}^t)$$

where k is the subject and t is the time period.

14. The system of claim 3, wherein said second axis comprises a High Blood Glucose Index (HBGI) of said blood glucose data.

15. The system of claim 14, wherein said High Blood Glucose Index (HBGI) is provided by:

$$HBGI_k^t = \frac{1}{n_k^t}\sum_{s=1}^{n_k^t} rh(x_{ks}^t)$$

where k is the subject and t is the time period.

16. The system of claim 5, wherein:
said first zone further comprises said first axis ranging from about less than 2.5 and said second axis ranging from about less than 5;

said second zone further comprises said first axis ranging from about 2.5-5 and said second axis ranging from about less than 5;

said third zone further comprises said first axis ranging from about less than 2.5 and said second axis ranging from about 5-10;

said fourth zone further comprises said first axis ranging from about 2.5-5 and said second axis ranging from about 5-10;

said fifth zone further comprises said first axis ranging from about greater than 5 and said second axis ranging from about less than 5;

said sixth zone further comprises said first axis ranging from about less than 2.5 and said second axis ranging from about greater than 10;

said seventh zone further comprises said first axis ranging from about greater than 5 and said second axis ranging from about 5-10;

said eighth zone further comprises said first axis ranging from about 2.5-5 and said second axis ranging from about greater than 10; and said ninth zone further comprises said first axis ranging from about greater than 5 and said second axis ranging from about greater than 10.

17. The system of claim 1, wherein said tracking determines extreme glucose events.

18. The system of claim 1, wherein said tracking determines the extent of glycemic fluctuations over a specified time interval.

19. The system of claim 1, wherein said tracking comprises plotting a trajectory of data points from said blood glucose data on a specified time interval.

20. The system of claim 1, wherein said blood glucose data is acquired from continuous glucose monitoring (CGM) or self-monitoring blood glucose (SMBG) or both.

21. A computer program product comprising a non-transitory computer useable medium having a computer program logic for enabling at least one processor in a computer system to track blood glucose variability in diabetes in a subject, or in a group of subjects, said computer program logic comprising:
acquiring a plurality of blood glucose data of the subject over a predefined period of time;
computing blood glucose variability of the subject over said predefined period of time using said blood glucose data;
plotting the computed blood glucose variability on an output display in the form of data points on a graph having a coordinate system representing hypoglycemic risk along one axis of said graph and hyperglycemic risk along another axis of said graph;
wherein the location of a data point in said coordinate system of said graph represents a variable degree of control of blood glucose levels of said subject; and
wherein said tracking provides an area of optimal glucose control in said graph, and provides areas in said graph indicating risk for hyperglycemia and hypoglycemia.

22. The computer program product of claim 21, wherein said coordinate system of said graph is transmitted to an interface.

23. The computer program product of claim 21, wherein said coordinate system of said graph comprises:
a first axis representing the risk for hypoglycemia; and
a second axis representing the risk for hyperglycemia.

24. The computer program product of claim 21, wherein said coordinate system of said graph comprises:
a first axis representing the Low Blood Glucose Index (LBGI); and
a second axis representing the High Blood Glucose Index (HBGI).

25. The computer program product of claim 21, wherein said coordinate system of said graph comprises:
a first axis representing the inverse-coded lower percentile; and
a second axis representing the upper percentile.

26. The computer program product of claim 21, wherein said coordinate system of said graph comprises at least one of:
a first zone representing the optimal control of glucose variability;
a second zone representing moderate deviations into hypoglycemia, but good control of hyperglycemia;
a third zone representing moderate deviations into hyperglycemia, but good control of hypoglycemia;
a fourth zone representing moderate deviations towards both hypoglycemia and hyperglycemia;
a fifth zone representing over-correction of hyperglycemia;
a sixth zone representing over-correction of hypoglycemia;
a seventh zone representing failure to deal with hypoglycemia;
an eighth zone representing failure to deal with hyperglycemia; and
a ninth zone representing an erroneous control.

27. The computer program product of claim 23, wherein said first axis comprises about the inverse-coded 2.5% of a distribution of said blood glucose data and the second axis comprises about the 97.5% of a distribution of said blood glucose data.

28. The computer program product of claim 23, wherein said first axis comprises about the 97.5% of a distribution of said blood glucose data and the second axis comprises about the inverse-coded 2.5% of a distribution of said blood glucose data.

29. The computer program product of claim 23, wherein:
said first zone further comprises said first axis ranging from about 110-80 mg/dl and said second axis ranging from about 110-200 mg/dl;
said second zone further comprises said first axis ranging from about 80-50 mg/dl and said second axis ranging from about 110-200 mg/dl;
said third zone further comprises said first axis ranging from about 110-80 mg/dl and said second axis ranging from about 200-400 mg/dl;
said fourth zone further comprises said first axis ranging from about 80-50 mg/dl and said second axis ranging from about 200-400 mg/dl;
said fifth zone further comprises said first axis ranging from about less than 50 mg/dl and said second axis ranging from about 110-200 mg/dl;
said sixth zone further comprises said first axis ranging from about 110-80 mg/dl and said second axis ranging from about greater than 400 mg/dl;
said seventh zone further comprises said first axis ranging from about less than 50 mg/dl and said second axis ranging from about 200-400 mg/dl;
said eighth zone further comprises said first axis ranging from about 80-50 mg/dl and said second axis ranging from about greater than 400 mg/dl; and
said ninth zone further comprises said first axis ranging from about less than 50 mg/dl and said second axis ranging from about greater than 400 mg/dl.

30. The computer program product of claim 25, wherein said first axis comprises about the inverse-coded 25% and the second axis comprises about the 75% of said blood glucose data.

31. The computer program product of claim 25, wherein said second axis comprises about the inverse-coded 25% and the first axis comprises about the 75% of said blood glucose data.

32. The computer program product of claim 25, wherein:
said first zone further comprises said first axis ranging from about 110-90 mg/dl and said second axis ranging from about 110-180 mg/dl;
said second zone further comprises said first axis ranging from about 90-70 mg/dl and said second axis ranging from about 110-180 mg/dl;
said third zone further comprises said first axis ranging from about 110-90 mg/dl and said second axis ranging from about 180-250 mg/dl;
said fourth zone further comprises said first axis ranging from about 90-70 mg/dl and said second axis ranging from about 180-250 mg/dl;
said fifth zone further comprises said first axis ranging from about less than 70 mg/dl and said second axis ranging from about 110-180 mg/dl;
said sixth zone further comprises said first axis ranging from about 110-90 mg/dl and said second axis ranging from about greater than 250 mg/dl;
said seventh zone further comprises said first axis ranging from about less than 70 mg/dl and said second axis ranging from about 180-250 mg/dl;
said eighth zone further comprises said first axis ranging from about 90-70 mg/dl and said second axis ranging from about greater than 250 mg/dl; and
said ninth zone further comprises said first axis ranging from about less than 70 mg/dl and said second axis ranging from about greater than 250 mg/d1.

33. The computer program product of claim 24, wherein said first axis comprises a Low Blood Glucose Index (LBGI) of said blood glucose data.

34. The computer program product of claim 33, wherein said Low Blood Glucose Index (LBGI) is provided by:

$$LBGI_k^t = \frac{1}{n_k^t} \sum_{s=1}^{n_k^t} rl(x_{ks}^t)$$

where k is the subject and t is the time period.

35. The computer program product of claim 34, wherein said second axis comprises a High Blood Glucose Index (HBGI) of said blood glucose data.

36. The computer program product of claim 25, wherein said High Blood Glucose Index (HBGI) is provided by:

$$HBGI_k^t = \frac{1}{n_k^t} \sum_{s=1}^{n_k^t} rh(x_{ks}^t)$$

where k is the subject and t is the time period.

37. The computer program product of claim 26, wherein:
said first zone further comprises said first axis ranging from about less than 2.5 and said second axis ranging from about less than 5;
said second zone further comprises said first axis ranging from about 2.5-5 and said second axis ranging from about less than 5;
said third zone further comprises said first axis ranging from about less than 2.5 and said second axis ranging from about 5-10;
said fourth zone further comprises said first axis ranging from about 2.5-5 and said second axis ranging from about 5-10;
said fifth zone further comprises said first axis ranging from about greater than 5 and said second axis ranging from about less than 5;
said sixth zone further comprises said first axis ranging from about less than 2.5 and said second axis ranging from about greater than 10;
said seventh zone further comprises said first axis ranging from about greater than 5 and said second axis ranging from about 5-10;
said eighth zone further comprises said first axis ranging from about 2.5-5 and said second axis ranging from about greater than 10; and
said ninth zone further comprises said first axis ranging from about greater than 5 and said second axis ranging from about greater than 10.

38. The computer program product of claim 21, wherein said tracking determines extreme glucose events.

39. The computer program product of claim 21, wherein said tracking determines the extent of glycemic fluctuations over a specified time interval.

40. The computer program product of claim 21, wherein said tracking comprises plotting a trajectory of data points from said blood glucose data on a specified time interval.

41. The computer program product of claim 21, wherein said blood glucose data is acquired from continuous glucose monitoring (CGM) or self-monitoring blood glucose (SMBG) or both.

42. The system of claim 18, wherein said specified time interval is approximately two or more days.

43. The system of claim 18, wherein said specified time interval is approximately a daily basis.

44. The system of claim 18, wherein said specified time interval is less than a daily basis.

45. The system of claim 18, wherein said specified time interval is approximately half a day.

46. The system of claim 18, wherein said specified time interval is approximately two or more hours.

47. The system of claim 18, wherein said specified time interval is approximately an hour.

48. The system of claim 18, wherein said specified time interval is less than an hour.

49. The system of claim 18, wherein said specified time interval is approximately fifteen minutes.

50. The computer program product of claim 39, wherein said specified time interval is approximately two or more days.

51. The computer program product of claim 39, wherein said specified time interval is approximately a daily basis.

52. The computer program product of claim 39, wherein said specified time interval is less than a daily basis.

53. The computer program product of claim 39, wherein said specified time interval is approximately half a day.

54. The computer program product of claim 39, wherein said specified time interval is approximately two or more hours.

55. The computer program product of claim 39, wherein said specified time interval is approximately an hour.

56. The computer program product of claim 39, wherein said specified time interval is less than an hour.

57. The computer program product of claim 39, wherein said specified time interval is approximately fifteen minutes.

* * * * *